(12) United States Patent
Shaikh et al.

(10) Patent No.: US 11,801,081 B2
(45) Date of Patent: Oct. 31, 2023

(54) SURGICAL INSTRUMENT AND METHOD

(71) Applicant: Warsaw Orthopedic, Inc., Warsaw, IN (US)

(72) Inventors: Zeeshan K. Shaikh, Sholapur (IN); Ryan M. Stevenson, Bulimba (AU)

( * ) Notice: Subject to any disclaimer, the term of this patent is extended or adjusted under 35 U.S.C. 154(b) by 0 days.

(21) Appl. No.: 17/519,165

(22) Filed: Nov. 4, 2021

(65) Prior Publication Data
US 2023/0136936 A1   May 4, 2023

(51) Int. Cl.
*A61B 17/80* (2006.01)
*A61B 17/88* (2006.01)
*A61B 17/70* (2006.01)

(52) U.S. Cl.
CPC ...... *A61B 17/8863* (2013.01); *A61B 17/7059* (2013.01); *A61B 17/7082* (2013.01)

(58) Field of Classification Search
CPC ...... A61B 17/80–8095; A61B 17/7059; A61B 17/8863
See application file for complete search history.

(56) References Cited

U.S. PATENT DOCUMENTS

| | | | |
|---|---|---|---|
| 4,474,046 A * | 10/1984 | Cook | B21D 7/063 72/413 |
| 5,113,685 A | 5/1992 | Asher et al. | |
| 5,490,409 A * | 2/1996 | Weber | B21D 7/022 72/409.1 |
| 5,819,580 A * | 10/1998 | Gauthier | A61B 17/8863 72/409.1 |
| 7,473,257 B2 | 1/2009 | Knopfle et al. | |
| 7,740,649 B2 | 6/2010 | Mosca et al. | |
| 8,419,745 B2 | 4/2013 | Sixto, Jr. et al. | |
| 8,454,665 B2 | 6/2013 | Sidebotham | |
| 9,427,275 B2 * | 8/2016 | Knoepfle | A61B 17/8863 |
| 9,839,463 B2 * | 12/2017 | Dominik | B21D 7/063 |
| 10,052,103 B2 | 8/2018 | Wahl et al. | |
| 10,702,323 B2 * | 7/2020 | Richards | A61B 17/8863 |
| 2009/0177239 A1 | 7/2009 | Castro | |
| 2009/0222020 A1 * | 9/2009 | Schmuck | A61B 17/8863 606/205 |
| 2010/0268119 A1 * | 10/2010 | Morrison | A61B 17/8863 600/587 |

(Continued)

FOREIGN PATENT DOCUMENTS

DE   102005029165 A1   1/2007
IT   201800005694 A1   11/2019

OTHER PUBLICATIONS

International Searching Authority—European Patent Office, P.B. 5818 Patentlaan 2, NL-2280 HV Rijswijk, International Search Report and Written Opinion of the International Searching Authority, International application No. PCT/182022/060642, dated Feb. 27, 2023 (Feb. 27, 2023).

*Primary Examiner* — Eduardo C Robert
*Assistant Examiner* — Steven J Cotroneo
(74) *Attorney, Agent, or Firm* — Sorell, Lenna & Schmidt, LLP

(57) ABSTRACT

A surgical instrument includes a first arm including a first support. A second arm includes a second support. A fulcrum defines an implant cavity with the supports. A member is selectively engageable with alternatively configured and/or dimensioned implants disposable in the implant cavity. Implants, spinal constructs and methods are disclosed.

20 Claims, 17 Drawing Sheets

(56) References Cited

U.S. PATENT DOCUMENTS

| | | | | |
|---|---|---|---|---|
| 2012/0047980 A1* | 3/2012 | Harper | ............... | B21D 7/024 |
| | | | | 72/199 |
| 2012/0247173 A1* | 10/2012 | Paris | ............... | A61B 17/8863 |
| | | | | 72/458 |
| 2017/0042597 A1* | 2/2017 | Rinner | ............... | A61B 17/8863 |
| 2019/0298428 A1 | 10/2019 | Richards et al. | | |

* cited by examiner

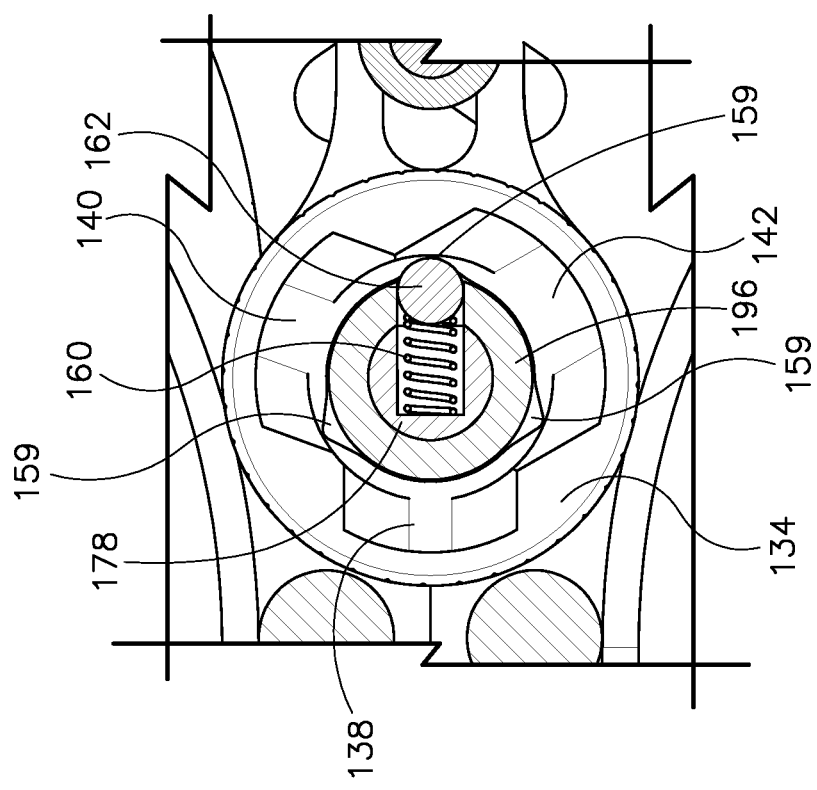
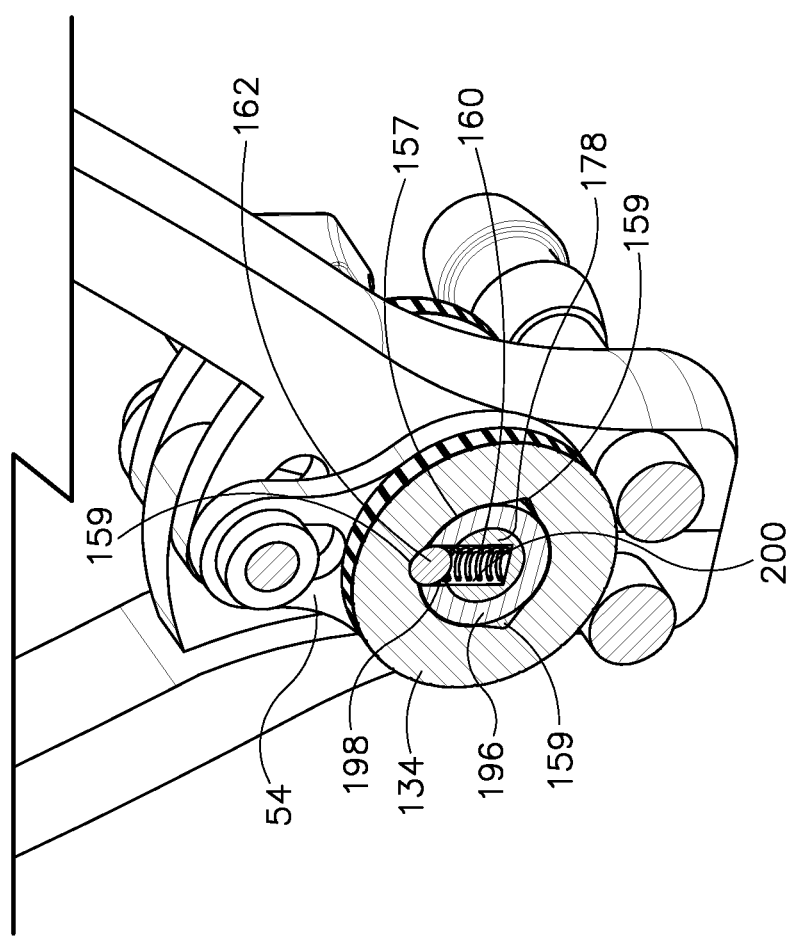
FIG. 8
FIG. 7

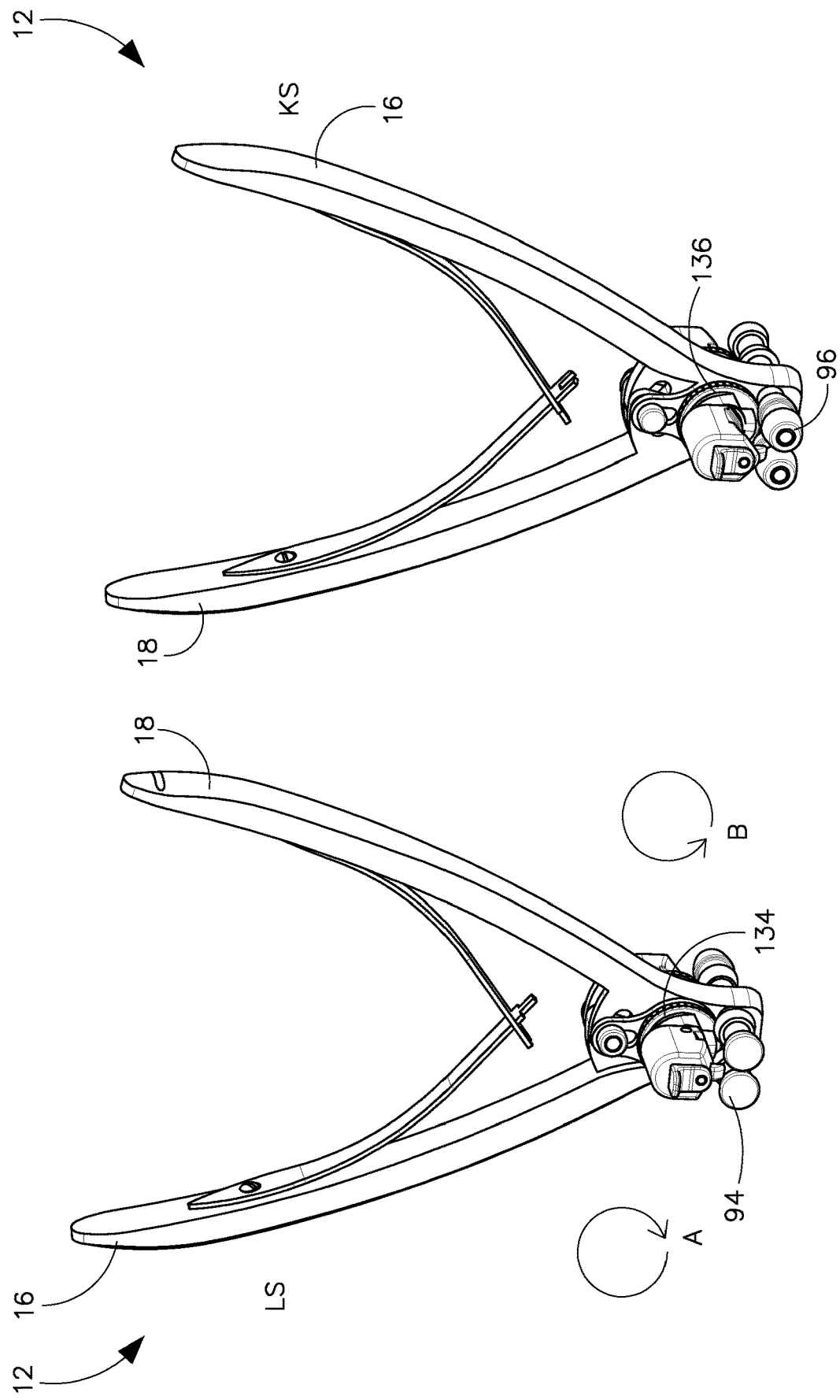

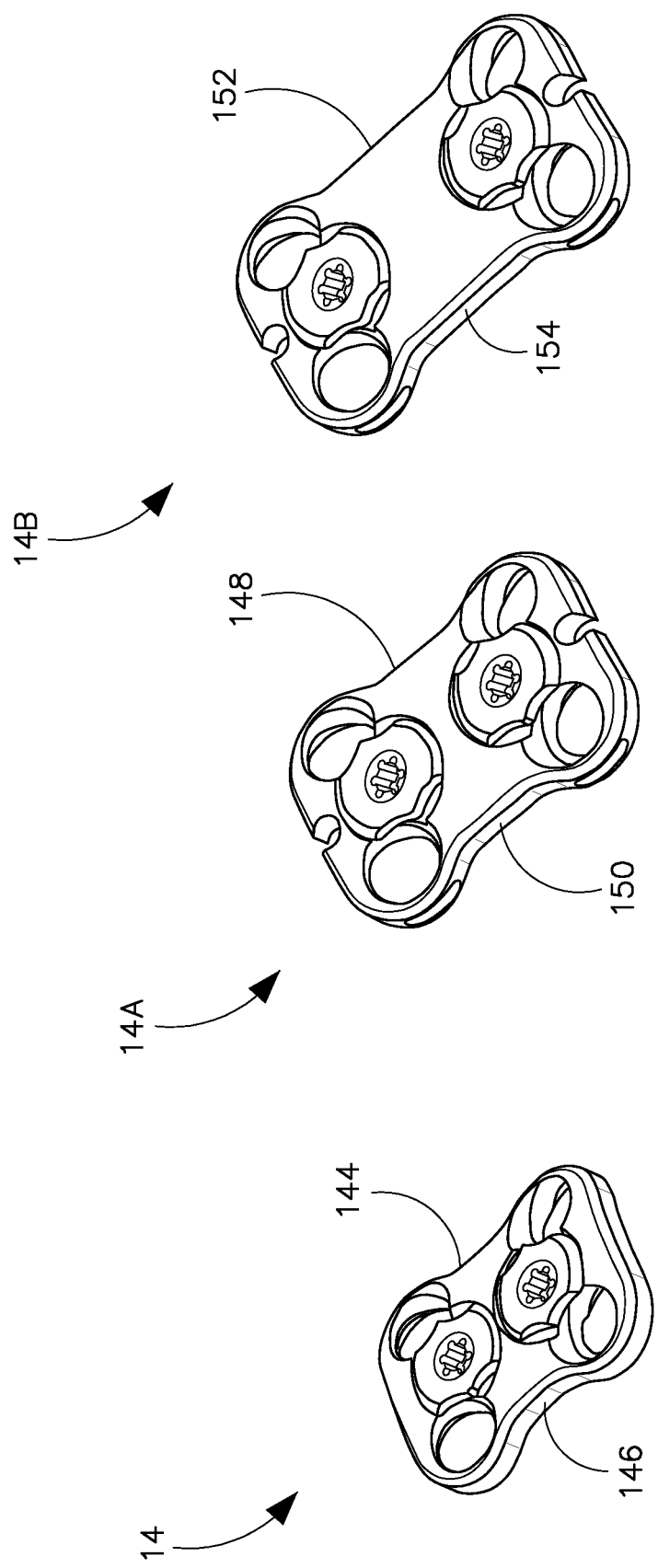

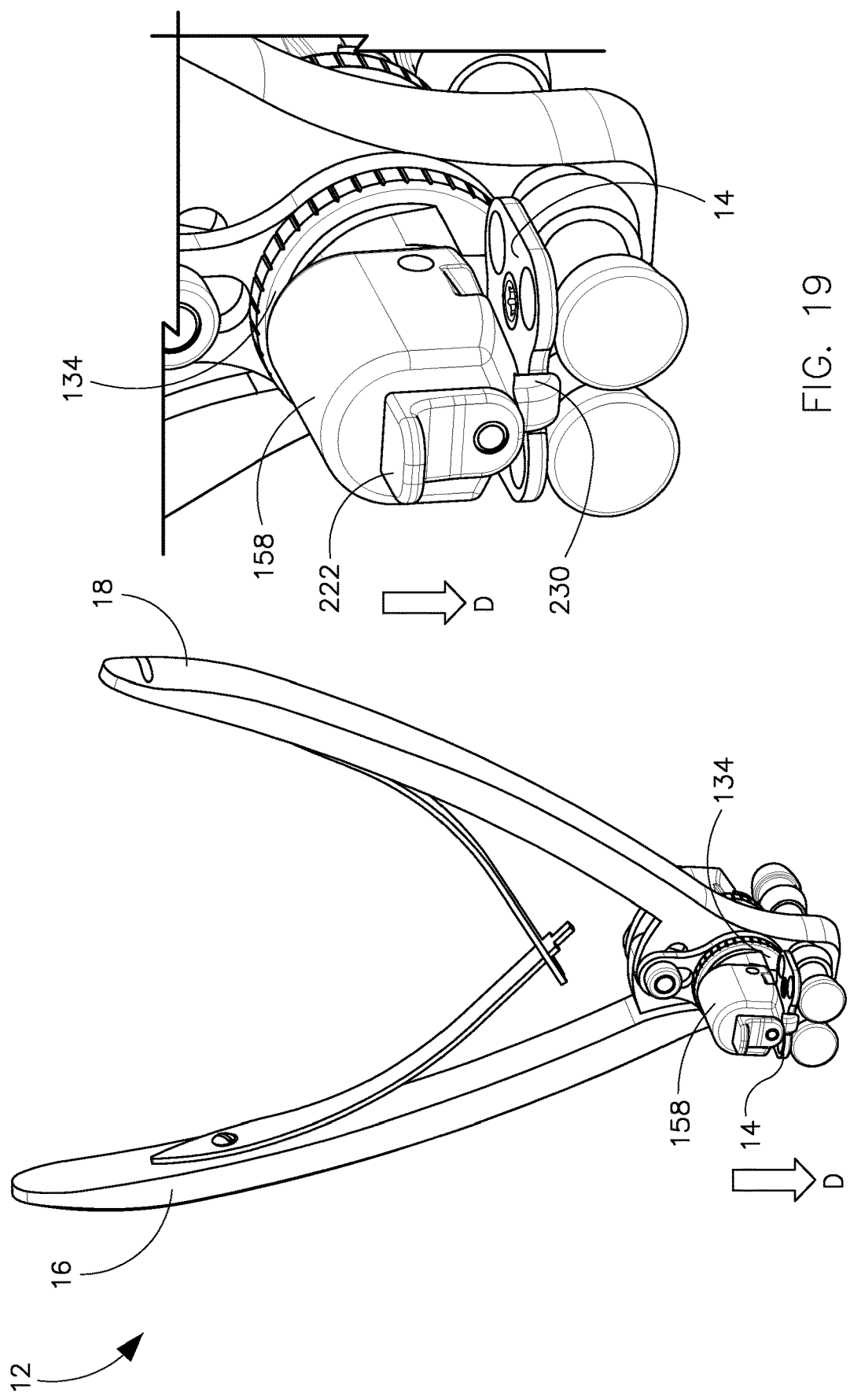

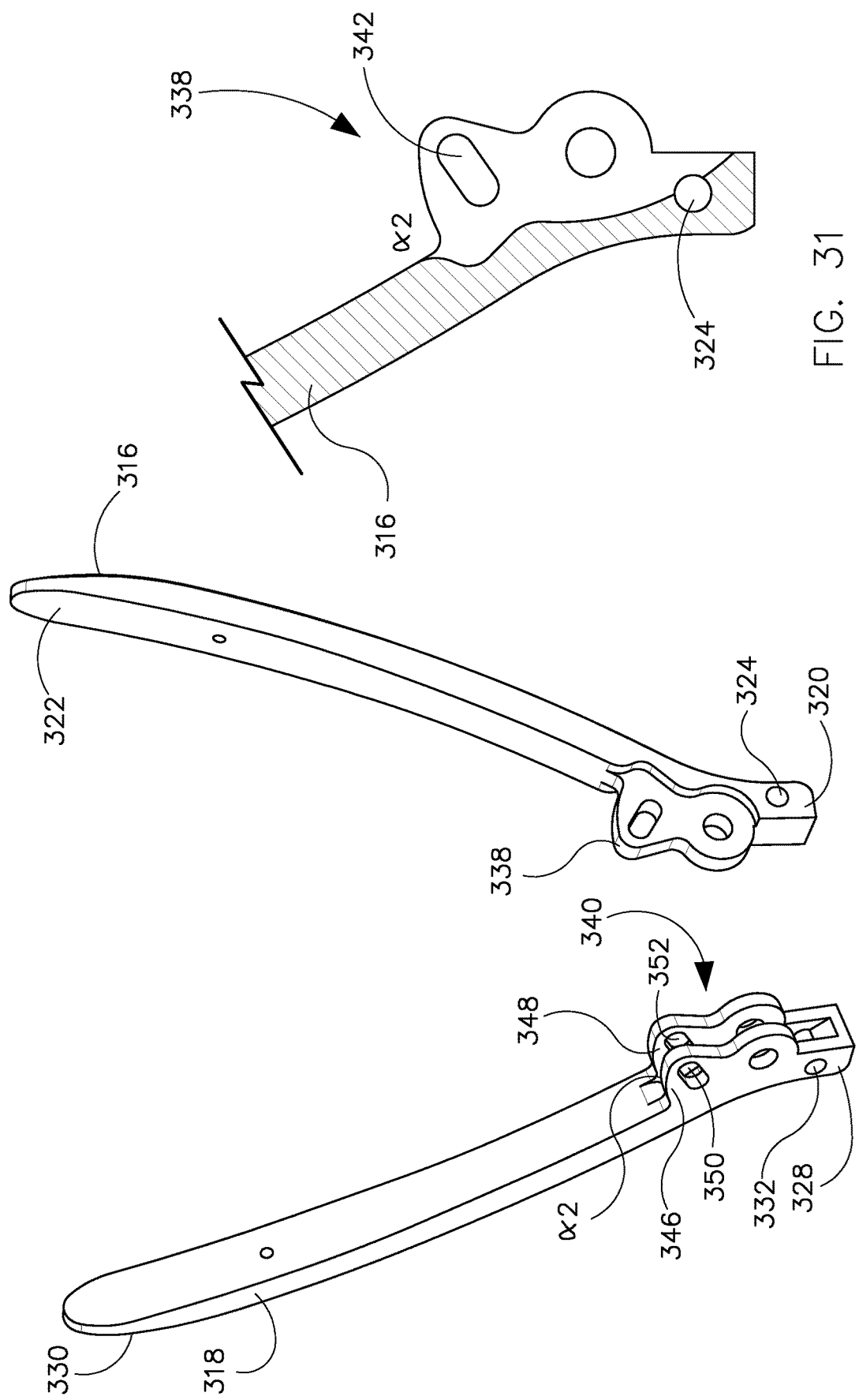

SURGICAL INSTRUMENT AND METHOD

TECHNICAL FIELD

The present disclosure generally relates to medical devices for the treatment of musculoskeletal disorders, and more particularly to a surgical system and a method for treating a spine that includes one or more instruments and implants disposed with vertebrae.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes discectomy, corpectomy, laminectomy, fusion, fixation, correction and implantable prosthetics. As part of these surgical treatments, implants such as bone fasteners, interbody devices, plates, connectors and vertebral rods are often used to provide stability to a treated region. These implants can redirect stresses away from a damaged or defective region while healing takes place to restore proper alignment and generally support the vertebral members. Surgical instruments are employed, for example, to engage the implants for attachment to the exterior of one or more vertebral members. This disclosure describes an improvement over these prior technologies.

SUMMARY

In one embodiment, a surgical instrument is provided. The surgical instrument includes a first arm including a first support. A second arm includes a second support. A fulcrum defines an implant cavity with the supports and includes a plurality of mating elements engageable with alternately configured and/or dimensioned implants. In some embodiments, implants, spinal constructs and methods are disclosed.

In one embodiment, the surgical instrument includes a first arm including a first support. A second arm is provided that includes a second support. A fulcrum defines an implant cavity with the supports and includes a releasable lock configured to be positioned in a locked orientation and a non-locked orientation.

In one embodiment, a surgical system is provided. The surgical system includes an instrument comprising a first arm including a first support. A second arm includes a second support. A fulcrum defines an implant cavity with the supports and includes an adjustable mating element. The surgical system includes a spinal plate engageable with the adjustable mating element.

BRIEF DESCRIPTION OF THE DRAWINGS

The present disclosure will become more readily apparent from the specific description accompanied by the following drawings, in which:

FIG. 7 is a break away view in part cross-section of the components shown in FIG. 1;

FIG. 8 is a break away view of the components shown in FIG. 1;

FIG. 10 is a perspective view of the components shown in FIG. 1;

FIG. 11 is a perspective view of the components shown in FIG. 1;

FIG. 12 is a perspective view of one embodiment of a surgical system in accordance with the principles of the present disclosure;

FIG. 13 is a perspective view of one embodiment of a surgical system in accordance with the principles of the present disclosure;

FIG. 14 is a perspective view of one embodiment of a surgical system in accordance with the principles of the present disclosure;

FIG. 18 is a perspective view of components of the system shown in FIG. 1;

FIG. 19 is a break away view of the components shown in FIG. 19;

FIG. 30 is a perspective view with parts separated of components shown in FIG. 29;

FIG. 31 is a break away cross-section view of components shown in FIG. 30; and

DETAILED DESCRIPTION

Figure 1:
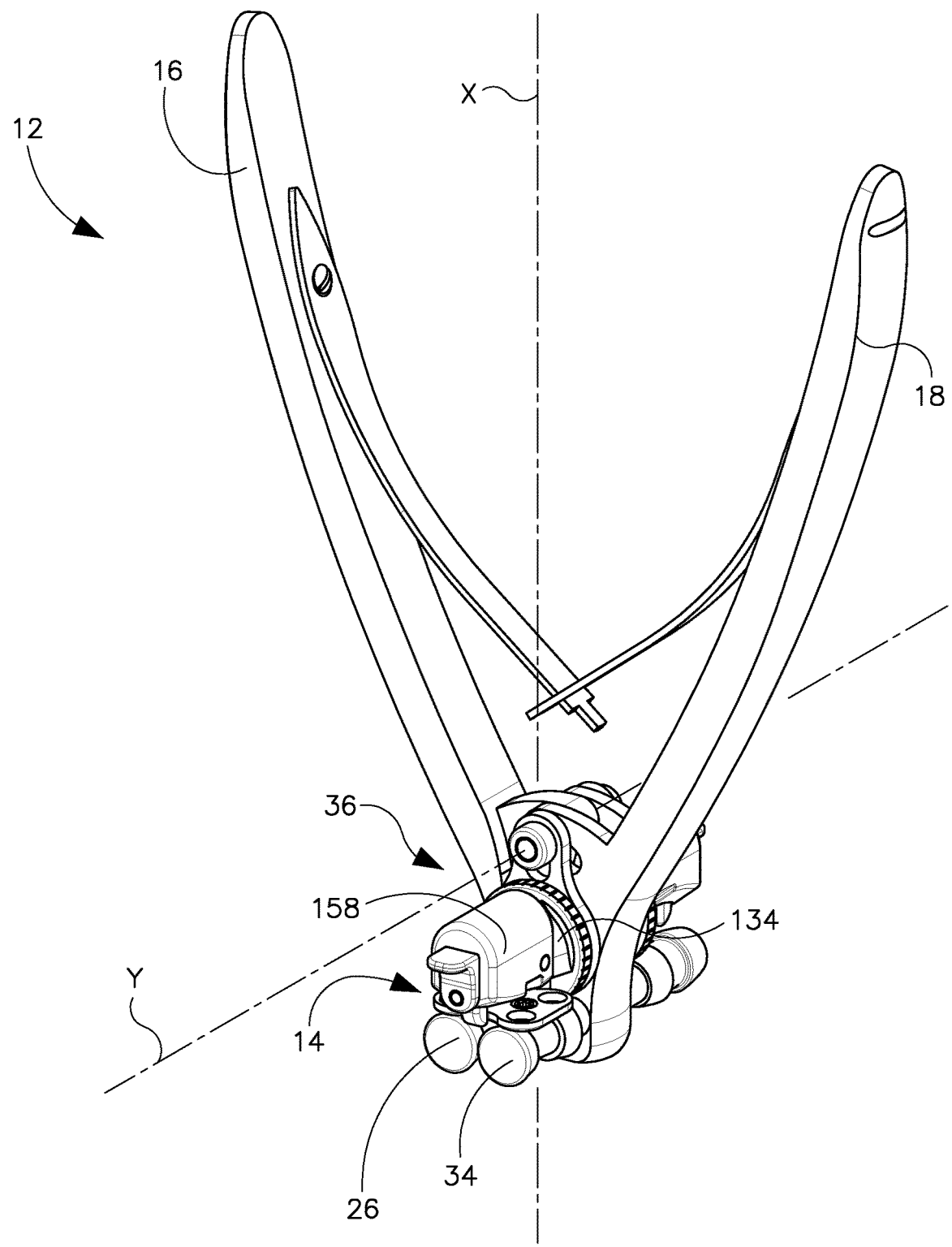
FIG. 1 is a perspective view of one embodiment of components of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical system and a method for treating a spine that includes a surgical instrument and one or more implants disposed with vertebrae. In some embodiments, the surgical system includes a surgical instrument, that is configured for contouring surgical implants, for example, spinal plates. In some embodiments, the surgical instrument comprises a surgical implant contouring instrument that contours a cervical plate by gradually increasing the amount of lordotic curvature or decreasing the amount of lordotic curvature of the plate. In some embodiments, the surgical implant contouring instrument includes a dial mechanism configured for use with one or more alternately configured and/or dimensioned spinal plates. In some embodiments, the dial mechanism includes a selective locking configuration. In some embodiments, the one or more plates may comprise components of a spinal implant system and/or kit. In some embodiments, the systems and methods of the present disclosure comprise surgical navigation and medical devices including surgical instruments and implants that are employed with a surgical treatment, as described herein, for example, with a cervical, thoracic, lumbar and/or sacral region of a spine.

In some embodiments, the present surgical system includes a surgical instrument, for example, a surgical implant contouring instrument configured for contouring spinal implants, for example, anterior cervical plates. In some embodiments, the surgical implant contouring instrument comprises a spinal plate bender employed with anterior cervical plates contoured to a selected section of a patient's anatomy, for example, a section of a spine for fixation. In some embodiments, the spinal plate bender is configured to contour an anterior cervical plate to a surface geometry of a spine for centering and retaining the plate to the spine.

In some embodiments, the present surgical system includes a surgical instrument, for example, a cervical plate bender. In some embodiments, the cervical plate bender is configured for contouring one or more alternatively configured and/or dimensioned spinal plates, for example, anterior cervical plates. In some embodiments, the cervical plate bender is configured to contour single level anterior cervical plates implemented in anterior cervical discectomy and fusion (ACDF) procedures. In some embodiments, the cervical plate bender includes a locking mechanism configured for use with one or more alternatively configured and/or dimensioned spinal plates. In some embodiments, the locking mechanism includes a central locking dial mechanism. In some embodiments, the cervical plate bender is configured to contour single level cervical plates with a central plane aligning mechanism. In some embodiments, the cervical plate bender includes a rotating dial mechanism configured to adjust the cervical plate bender for implementation with one or more alternatively configured and/or dimensioned spinal plates. In some embodiments, the one or more alternatively configured and/or dimensioned spinal plates include varying lengths. In some embodiments, the spinal plate includes a cervical plate for use in a single vertebral level. In some embodiments, the cervical plate includes a dimension of 19 mm in length. In some embodiments, the cervical plate includes a dimension of 21 mm in length. In some embodiments, the cervical plate includes a dimension of 23 mm in length.

In some embodiments, the present surgical implant contouring instrument is configured to contour a plate to increase or decrease lordosis of the plate. In some embodiments, a surface of the surgical implant contouring instrument is configured to increase lordosis of a plate, and a surface of the surgical implant contouring instrument is configured to decrease lordosis of the plate. In some embodiments, the surface of the surgical implant contouring instrument that increases lordosis of the plate is disposed on a side of the surgical implant contouring instrument, and the surface of the surgical implant contouring instrument that decreases lordosis of the plate is disposed on an opposing side of the surgical implant contouring instrument. In some embodiments, the surgical implant contouring instrument includes a pair of arms. In some embodiments, the surgical implant contouring instrument includes a pair of orientation control discs, a central disc locking pin and nut, a pair of dials, a central block to increase lordosis, a central block to decrease lordosis, a pair of 3 mm diameter balls, a set of four compression springs, a central block locking pin, a pair of plate locking pins, a pair of pull buttons, a pair of pins, a pair of bottom rollers to increase lordosis, a pair of bottom rollers to decrease lordosis, and/or a pair of flat springs.

In some embodiments, the present surgical implant contouring instrument is configured for contouring an anterior cervical plate. In some embodiments, the anterior cervical plate does not include a lordotic curve pre-manufactured into the anterior cervical plate. In some embodiments, the surgical implant contouring instrument is configured to contour the anterior cervical plate to gradually increase a selected amount of lordotic curvature or decrease a selected amount of lordotic curvature. In some embodiments, the surgical implant contouring instrument is configured to lock a plate with the locking mechanism at a central position on the surgical implant contouring instrument to align with a central plane of the plate to contour the plate for lordotic curvature. In some embodiments, locking the plate with the surgical implant contouring instrument enables a plate with selected dimensions and/or a single vertebral level cervical plate to be locked in place, avoiding the need for a user, for example, a surgeon to manually check central alignment of the plate. In some embodiments, the plate is locked with the surgical implant contouring instrument to avoid manually holding the plate in position with the surgical implant contouring instrument and to avoid slippage of the plate during contouring.

In some embodiments, the present surgical implant contouring instrument is configured for single vertebral level plate contouring. In some embodiments, the surgical implant contouring instrument includes a block configured for increasing lordosis of a plate and a block configured for decreasing lordosis of a plate. In some embodiments, each block is centrally disposed on the surgical implant contouring instrument. In some embodiments, each block is V-shaped. In some embodiments, the surgical implant contouring instrument is configured to contour plates at a minimum bend curvature required for plates that include a cap assembly. In some embodiments, the surgical implant contouring instrument includes a grooved central block and rollers configured for disposal with a plate. In some embodiments, locking caps are configured for disposal with the blocks and rollers. In some embodiments, the surgical implant contouring instrument includes a locking mechanism configured to secure a plate at a central orientation on the surgical implant contouring instrument during contouring. In some embodiments, the surgical implant contouring instrument engages with a lateral milled cutout face of the plate. In some embodiments, the face of the plate is flush with the dial of the surgical implant contouring instrument. In some embodiments, the dial mechanism engages with a ball and spring. In some embodiments, a plate contouring setting is selected for use with a selected plate size and the dial mechanism is rotated to the selected plate contouring setting. In some embodiments, the user can select from multiple plate contouring settings each configured for contouring a selected plate size. In some embodiments, the multiple plate contouring settings of the dial mechanism includes three plate size options. In some embodiments, the surgical implant contouring instrument is configured to contour a plate efficiently and is configured to reduce human error. In some embodiments, the surgical implant contouring instrument is configured to maintain plate alignment during plate contouring and avoids the need for a user to maintain visual and manual plate alignment. In some embodiments, the surgical implant contouring instrument is configured for use with a single vertebral level or multi vertebral level cervical plate system. In some embodiments, the surgical implant contouring instrument is configured for use with various spinal plate configurations, for example, lumbar, cervical, thoracic, sacral and/or pelvic.

In some embodiments, the present surgical system includes a surgical instrument, including a surgical implant contouring instrument that is employed with a method for contouring a plate to increase or decrease lordosis of the plate, the method includes the step of positioning the surgical implant contouring instrument in an open orientation. In some embodiments, in the open orientation, a pair of handle arms are spaced apart relative to each other. In some embodiments, the method includes the step of selecting a plate size for contouring. In some embodiments, the plate size includes 19 mm, 21 mm or 23 mm. In some embodiments, a dial mechanism of the surgical implant contouring instrument is rotated in a direction, for example clockwise or anti-clockwise until a selected plate size indicia, for example, a marking is aligned into a contour position. In some embodiments, the dial mechanism auto locks into one of the three size orientations via a ball and spring mechanism. In some embodiments, the ball and spring mechanism engages with the dial mechanism to prevent unintentional movement of the dial mechanism during use. In some embodiments, the method includes the step of contouring the plate to increase or decrease lordotic angle of the plate. In some embodiments, the plate is inserted into a selected side of the surgical implant contouring instrument that is specific to either increasing or decreasing the lordotic angle of the plate. In some embodiments, each side of the surgical implant contouring instrument, for example, on an arm of the surgical implant contouring instrument, is laser marked with indicia that indicates a side for increasing lordosis or decreasing lordosis of the plate. In some embodiments, the indicia includes text. In some embodiments, the plate is a cervical plate. In some embodiments, the method includes the step of inserting the plate into a selected side of the surgical implant contouring instrument. In some embodiments, a lock button is translated in a direction to insert the plate onto a central block of the surgical implant contouring instrument. In some embodiments, the method includes the step of releasing the lock button. In some embodiments, the user visually confirms that the lock button is fully released into its original orientation. In some embodiments, the plate is adjusted for engagement at a back side of the block. In some embodiments, the method includes the step of positioning the surgical implant contouring instrument in a closed orientation to contour the plate to a selected curvature/angle to increase lordosis. In some embodiments, the arms are manually translated towards each other for contouring. In some embodiments, the arms are manually translated towards each other and translation is prevented when the desired curvature of the plate is reached. In some embodiments, the surgical implant contouring instrument includes a stop element that prevents the surgical implant contouring instrument from contouring the plate more than 20 degrees. In some embodiments, the surgical implant contouring instrument contours the plate from 1 degree to 30 degrees. In some embodiments, to decrease lordosis, the method steps described above are repeated on the side of the surgical implant contouring instrument specific to decreasing the lordotic angle of the plate.

In one embodiment, one or all of the components of the surgical system are disposable, peel-pack, pre-packed sterile devices used with an implant. One or all of the components of the surgical system may be reusable. The surgical system may be configured as a kit with multiple sized and configured components.

In some embodiments, the present disclosure may be employed to treat spinal disorders, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-28, there is illustrated components of a surgical system 10 in accordance with the principles of the present disclosure.

The components of surgical system 10 can be fabricated from biologically acceptable materials suitable for medical applications, including metals, synthetic polymers, ceramics and bone material and/or their composites, depending on the particular application and/or preference of a medical practitioner. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 is employed, for example, with a minimally invasive procedure, including percutaneous techniques, mini-open and open surgical techniques to deliver and introduce an implant, for example, spinal plate 14, 14A and/or 14B at a surgical site within a body of a patient, for example, a section of a spine. Surgical system 10 includes a surgical instrument, for example, an implant contouring instrument 12 that is employed, for example, to contour an implant, for example, plate 14, 14A and/or 14B during a surgical treatment to the configuration and/or dimension of the spine. In some embodiments, the contour can include adjustment and/or correction of the components of surgical system 10 including, for example, increasing or decreasing lordosis, as described herein. In some embodiments, lordosis is increased from 1 to 20 degrees and kyphosis is decreased from 1 to 20 degrees, as described herein. In some embodiments, contour/contouring can include deforming, shaping, bending and/or conforming plate 14, 14A and/or 14B to increase or decrease lordosis.

Figure 2:
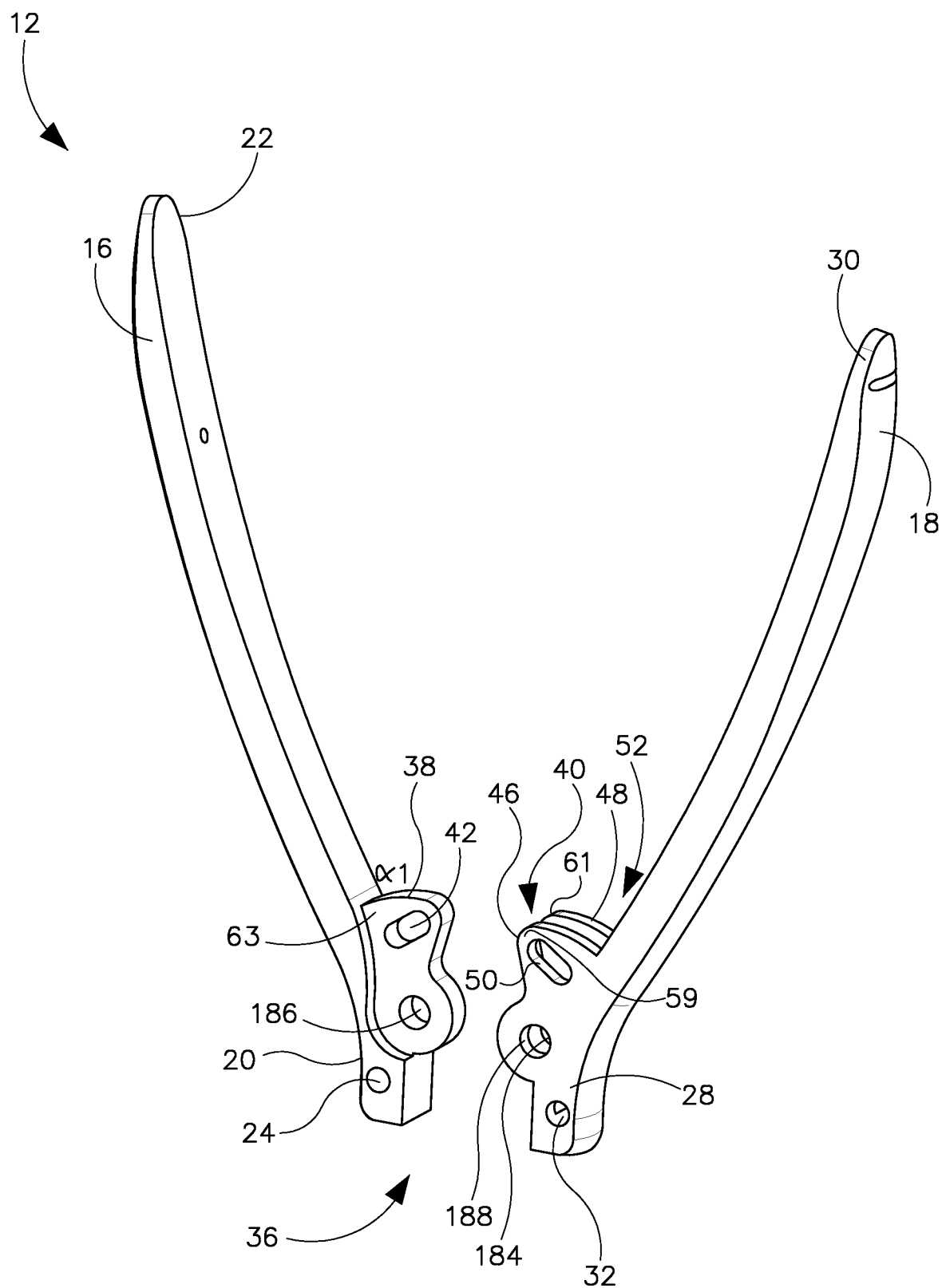
FIG. 2 is a perspective view with parts separated of the components shown in FIG. 1.
Figure 3:
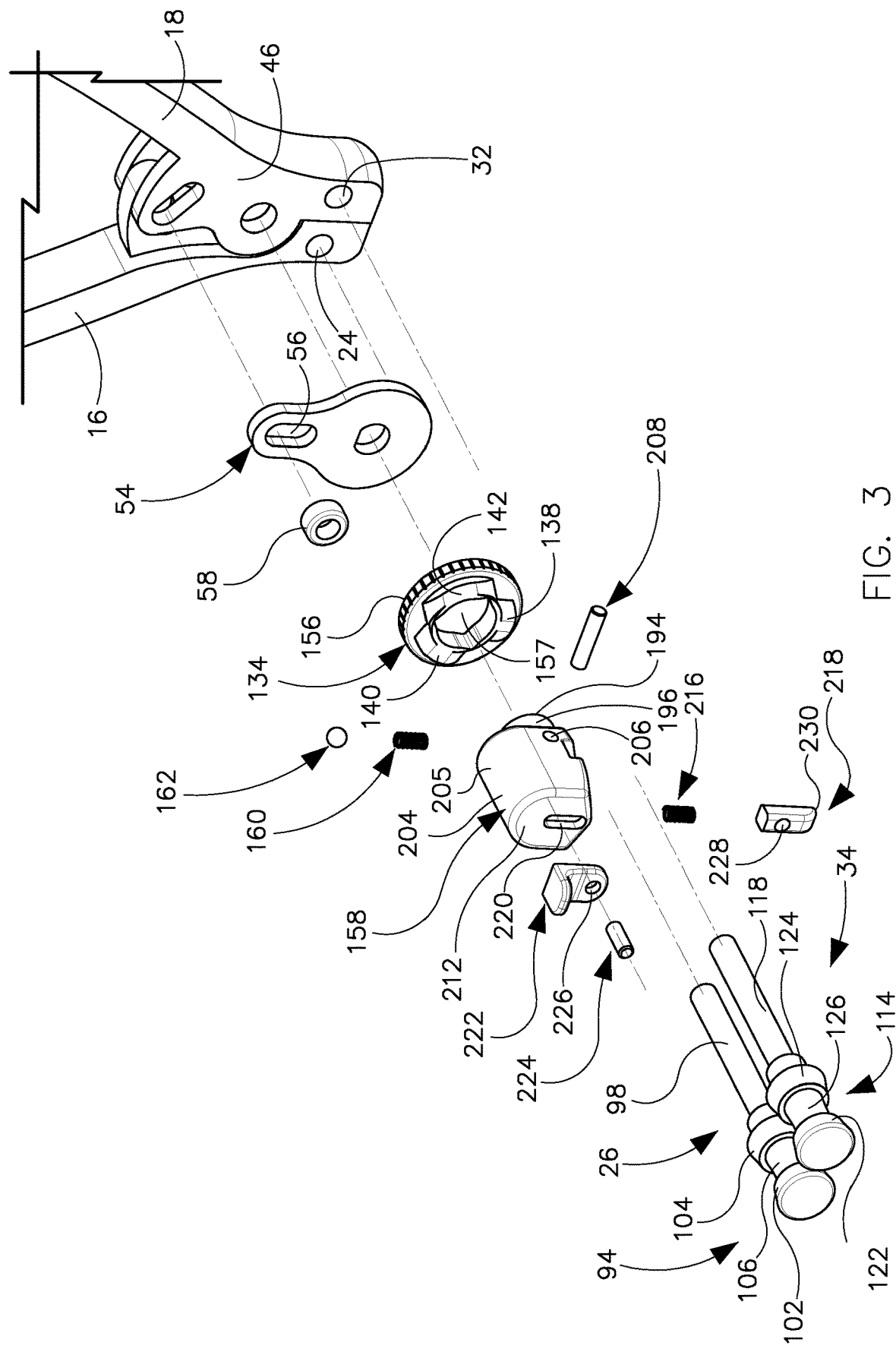
FIG. 3 is a perspective view with parts separated of the components shown in FIG. 1.

Implant contouring instrument 12 defines a longitudinal axis X, as shown in FIG. 1 and includes an arm 16 and an arm 18, as shown in FIG. 2. Arms 16, 18 are configured to be pivotable between an open orientation and a closed orientation relative to each other to move a fulcrum 36 of implant contouring instrument 12 to facilitate contouring of plate 14, 14A or 14B as described herein. Arm 16 extends between an end 20 and an end 22. End 20 includes a surface that defines an opening 24 configured for disposal of a portion of a support, for example, a portion of a transverse roller 26, as shown in FIG. 3 and described herein. In some embodiments, arm 16 may comprise overall and/or cross-section configurations, for example, cylindrical, round, oval, rectangular, polygonal, irregular, tapered, offset, staggered, uniform and non-uniform. In some embodiments, one or more of the surfaces of arm 16 may have alternate surface configurations, for example, rough, threaded for connection with surgical instruments, arcuate, undulating, porous, semi-porous, dimpled, polished and/or textured. In some embodiments, all or only a portion of arm 16 may be disposed at various orientations, relative to axis X, for example, transverse, perpendicular and/or other angular orientations such as acute or obtuse, co-axial and/or may be offset or staggered.

Arm 18 extends between an end 28 and an end 30. End 28 includes a surface that defines an opening 32 configured for disposal of a portion of a support, for example, a portion of a transverse roller 34, as shown in FIG. 3 and described herein. In some embodiments, arm 18 may comprise overall and/or cross-section configurations, for example, cylindrical, round, oval, rectangular, polygonal, irregular, tapered, offset, staggered, uniform and non-uniform. In some embodiments, one or more of the surfaces of arm 18 may have alternate surface configurations, for example, rough, threaded for connection with surgical instruments, arcuate, undulating, porous, semi-porous, dimpled, polished and/or textured. In some embodiments, all or only a portion of arm 18 may be disposed at various orientations, relative to axis X, for example, transverse, perpendicular and/or other angular orientations such as acute or obtuse, co-axial and/or may be offset or staggered.

Figure 4:
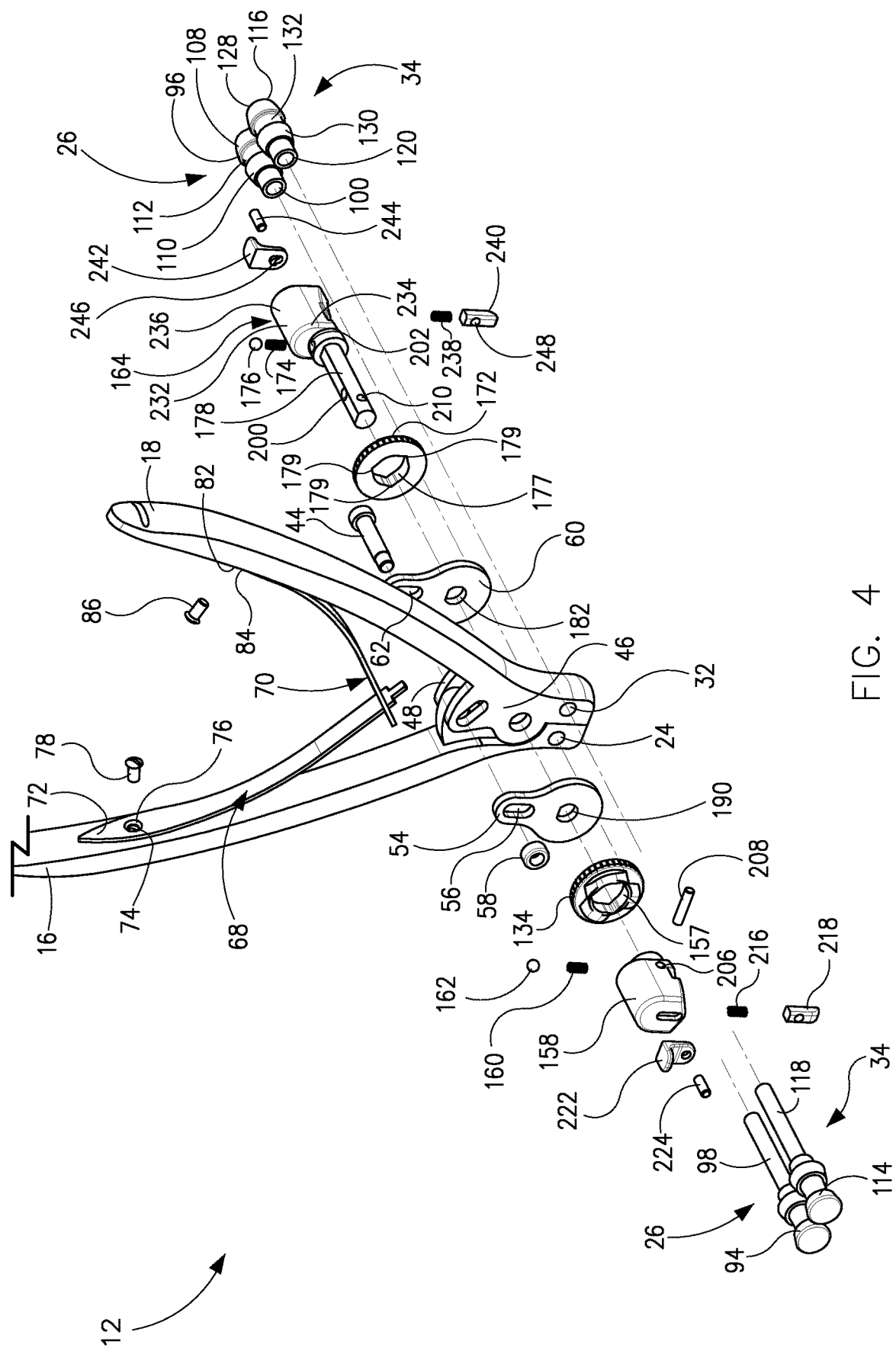
FIG. 4 is a perspective view with parts separated of the components shown in FIG. 1.
Figure 5:
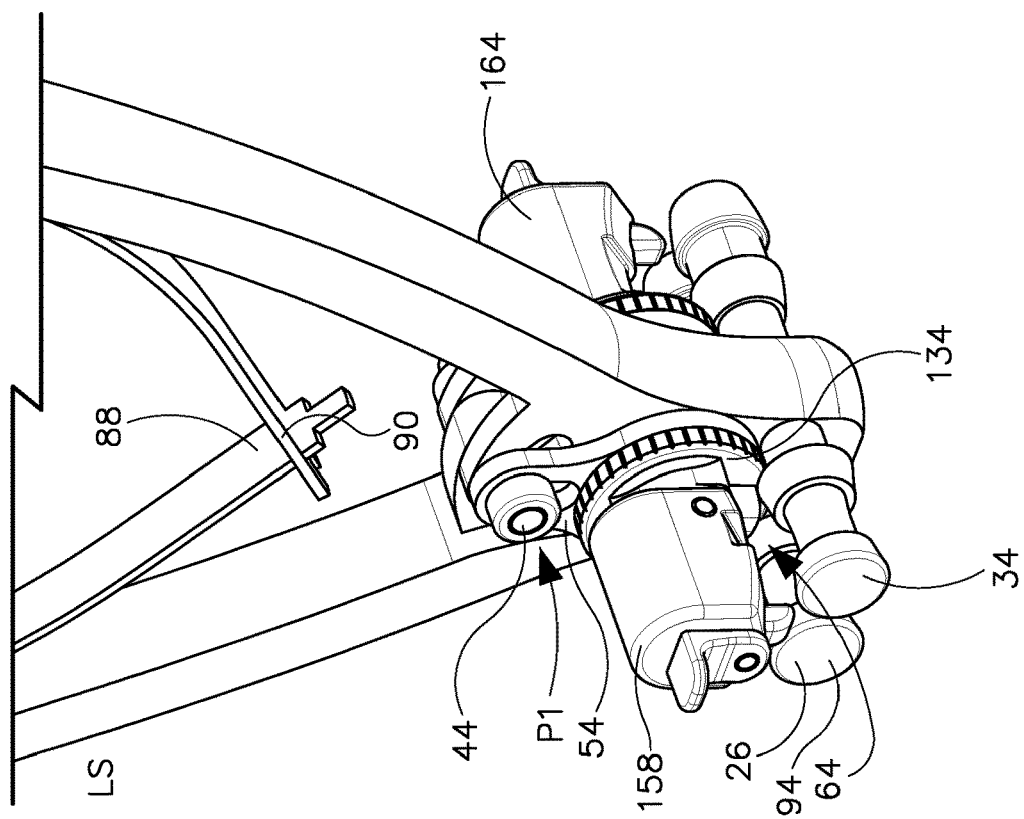
FIG. 5 is a break away view of components of the system shown in FIG. 1.

Fulcrum 36 defines a longitudinal axis Y, as shown in FIG. 1 and is configured to translate relative to transverse rollers 26, 34 to engage plate 14, 14A or 14B and to contour plate 14, 14A or 14B to a selected lordosis and/or kyphosis. Fulcrum 36 includes a link 38 defined from a surface of arm 16, as shown in FIG. 2. Link 38 is configured for disposal within a slot 40 of arm 18, as described herein for pivotable engagement between arms 16, 18. Link 38 includes a surface that defines an opening 42. Opening 42 is configured for disposal with a pin 44 of fulcrum 36, as shown in FIG. 4. Fulcrum 36 includes a link 46 and a link 48 defined from surfaces of arm 18, as shown in FIG. 2. Link 46 is parallel relative to link 48. Slot 40 is defined from an interior of links 46, 48. Link 46 includes a surface that defines an opening 50 and link 48 includes a surface that defines an opening 52. Openings 50, 52 are configured for disposal with pin 44, as shown in FIGS. 4 and 5. Links 38, 46 and 48 are disposed at an angle α1 to facilitate contouring plate 14, 14A or 14B at an angle from 1 degree to 20 degrees, as shown in FIG. 2. In some embodiments, links 46, 48 may comprise overall and/or cross-section configurations, for example, cylindrical, round, oval, rectangular, polygonal, irregular, tapered, offset, staggered, uniform and non-uniform.

Figure 25:
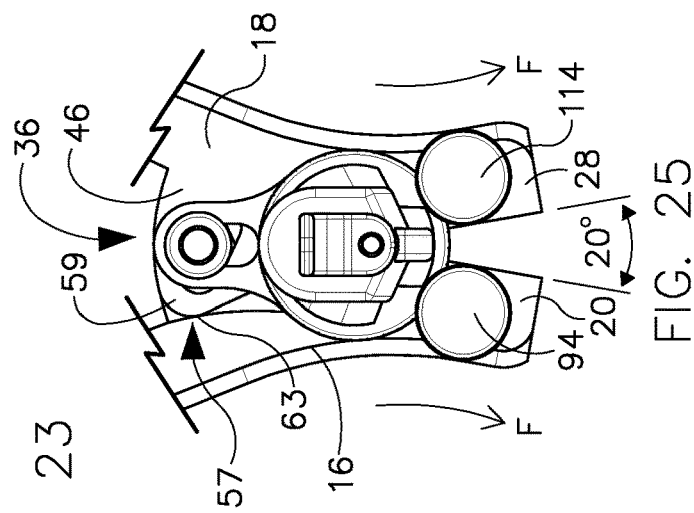
FIG. 25 is a break away view of components shown in FIG. 22.
Figure 23:
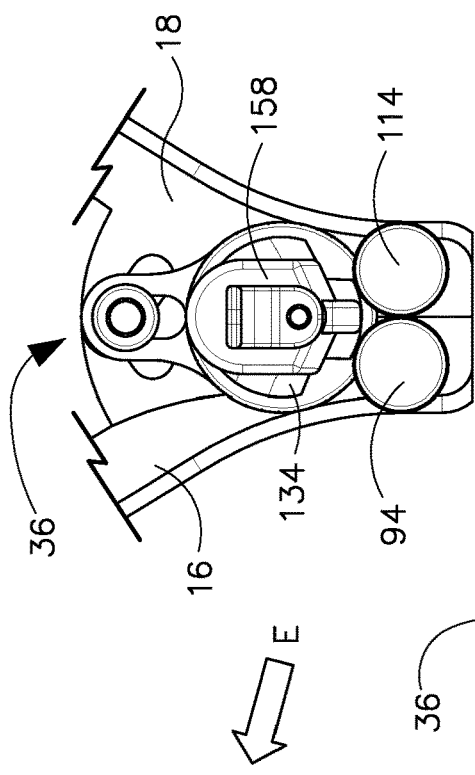
FIG. 23 is a break away view of components shown in FIG. 22.

Fulcrum 36 includes a disc 54, as shown in FIG. 3. Disc 54 is configured for engagement with a surface of link 46, as shown in FIGS. 3 and 4. Disc 54 includes a surface that defines an opening 56. Opening 56 is configured engagement with pin 44 and a nut 58. Fulcrum 36 includes a disc 60, as shown in FIG. 4. Disc 60 is configured for engagement with a surface of link 48, as shown in FIG. 4. Disc 60 includes a surface that defines an opening 62. Opening 62 is configured for disposal with pin 44. Pin 44 is disposable and translatable within openings 42, 50, 52, 56 and 62, and disposable with nut 58 to form a pivot P1, as shown in FIG. 5. Arms 16, 18 are movable between the open orientation and the closed orientation to translate fulcrum 36 via pivot P1 relative to transverse rollers 26, 34 to engage and contour plate 14, 14A or 14B to a selected lordosis and/or kyphosis. In some embodiments, lordosis is increased from 1 to 20 degrees and kyphosis is decreased from 1 to 20 degrees. A stop element 57 is defined from surfaces 59, 61 of links 46, 48 and a surface 63 of link 32, as shown in FIGS. 2 and 25. Stop element 57 is configured to limit implant contouring instrument 12 from contouring plate 14, 14A or 14B beyond 20 degrees.

Figure 6:
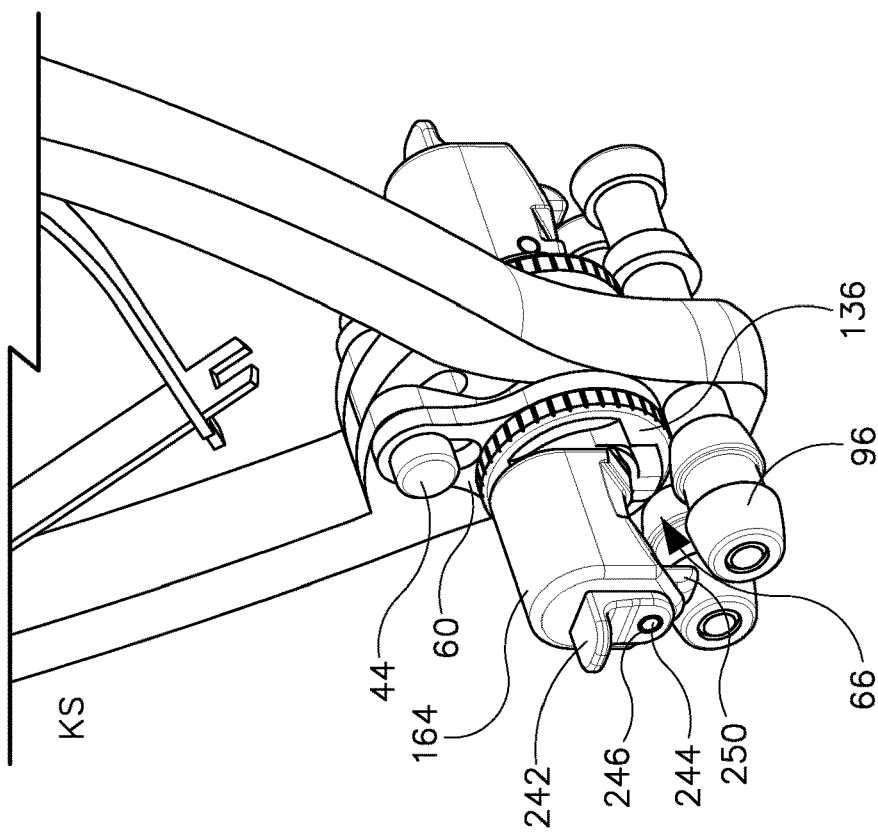
FIG. 6 is a break away view of components of the system shown in FIG. 1.

Fulcrum 36 defines an implant cavity 64 with transverse rollers 26, 34 on a lordosis surface (LS) of implant contouring instrument 12, as shown in FIG. 5, and an implant cavity 66 on a kyphosis surface (KS) of implant contouring instrument 12, as shown in FIG. 6. Arm 16 and/or arm 18 includes indicia, for example, laser markings including text that indicates the KS or the LS of implant contouring instrument 12, as shown in FIGS. 10 and 11. In some embodiments, the LS is a side of implant contouring instrument 12 and the KS is an opposing side of implant contouring instrument 12.

Figure 9:
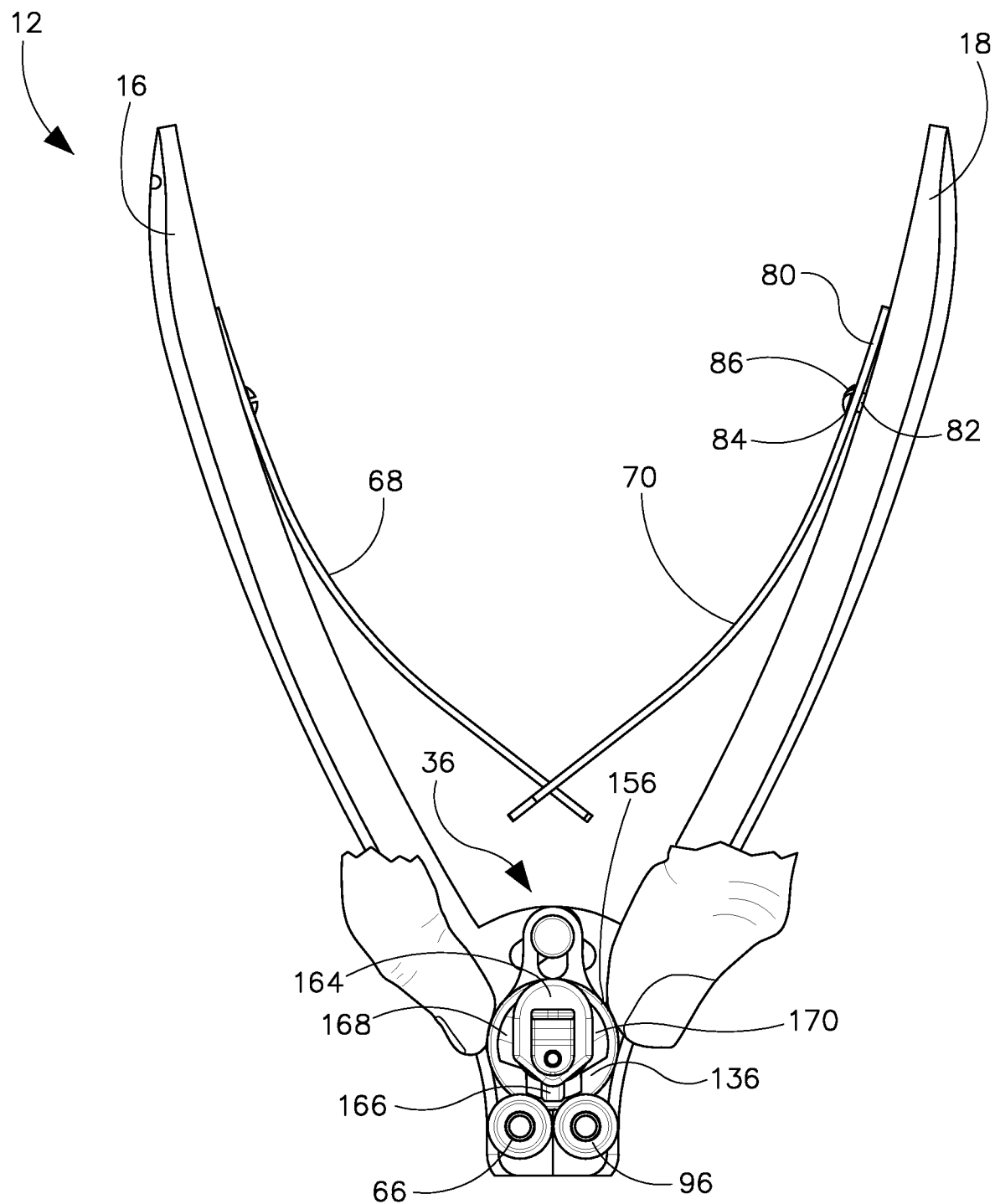
FIG. 9 is a front view of the components shown in FIG. 1.

Arms 16, 18 are biased to the open orientation via a pair of springs, for example, flat springs 68, 70, as shown in FIG. 4. An end 72 of spring 68 is configured for fixed engagement with a portion of arm 16. An inner surface of arm 16 defines an opening 74 that is configured for engagement with an opening 76 of end 72 and disposal of a pin 78, as shown in FIG. 4. An end 80 of spring 70 is configured for fixed engagement with a portion of arm 18. An inner surface of arm 18 defines an opening 82 that is configured for engagement with an opening 84 of end 80 and disposal of a pin 86, as shown in FIG. 9. Springs 68, 70 matingly engage at ends 88, 90, as shown in FIG. 5.

Transverse roller 26 includes a surface 94 and a surface 96, as shown in FIGS. 3-6. An intermediate portion 98 is disposed between surface 94 and surface 96 and is configured for disposal with opening 24 of arm 16, as shown in FIGS. 2-4. Surface 94 is monolithic with intermediate portion 98, and intermediate portion 98 is configured for disposal with an opening 100 of surface 96, as shown in FIG. 4. In some embodiments, intermediate portion 98 is monolithic with surface 94 and surface 96. Surface 94 includes arcuate portions 102, 104 and a planar portion 106 configured for engagement with plate 14, 14A or 14B to facilitate contouring of plate 14, 14A or 14B as shown in FIG. 3 and described herein. In some embodiments, surface 94 may comprise overall and/or cross-section configurations, for example, cylindrical, round, oval, rectangular, polygonal, irregular, tapered, offset, staggered, uniform and non-uniform. In some embodiments, surface 94 includes a lordosis surface.

Surface 96 includes arcuate portions 108, 110 and a planar portion 112 configured for engagement with plate 14, 14A or 14B to facilitate contouring of plate 14, 14A or 14B as shown in FIG. 4 and described herein. In some embodiments, surface 96 may comprise overall and/or cross-section configurations, for example, cylindrical, round, oval, rectangular, polygonal, irregular, tapered, offset, staggered, uniform and non-uniform. In some embodiments, surface 96 includes a kyphosis surface. In some embodiments, transverse roller 26 may include various surface configurations, for example, rough, friction, arcuate, undulating, mesh, porous, semi-porous, dimpled and/or textured according to the requirements of a particular application.

Transverse roller 34 includes a surface 114 and a surface 116, as shown in FIGS. 3-6. An intermediate portion 118 is disposed between surface 114 and surface 116 and is configured for disposal with opening 32 of arm 18, as shown in FIGS. 2-4. Surface 114 is monolithic with intermediate portion 118, and intermediate portion 118 is configured for disposal with an opening 120 of surface 116, as shown in FIG. 4. In some embodiments, intermediate portion 118 is monolithic with surface 114 and surface 116. Surface 114 includes arcuate portions 122, 124 and a planar portion 126 configured for engagement with plate 14, 14A or 14B to facilitate contouring of plate 14, 14A or 14B as shown in FIG. 3 and described herein. In some embodiments, surface 114 may comprise overall and/or cross-section configurations, for example, cylindrical, round, oval, rectangular, polygonal, irregular, tapered, offset, staggered, uniform and non-uniform. In some embodiments, surface 114 includes a lordosis surface.

Surface 116 includes arcuate portions 128, 130 and a planar portion 132 configured for engagement with plate 14, 14A or 14B to facilitate contouring of plate 14, 14A or 14B, as shown in FIG. 4 and described herein. In some embodiments, surface 116 may comprise overall and/or cross-section configurations, for example, cylindrical, round, oval, rectangular, polygonal, irregular, tapered, offset, staggered, uniform and non-uniform. In some embodiments, surface 116 includes a kyphosis surface. In some embodiments, transverse roller 34 may include various surface configurations, for example, rough, friction, arcuate, undulating, mesh, porous, semi-porous, dimpled and/or textured according to the requirements of a particular application.

Implant contouring instrument 12 includes a member, for example, a rotatable dial 134 disposed on the LS of implant contouring instrument 12 and a rotatable dial 136 disposed on the KS of implant contouring instrument 12, as shown in FIGS. 3-6. Rotatable dials 134, 136 are configured to be selectively engageable with alternatively configured and/or dimensioned implants, for example, implants 14, 14A and 14B disposable within implant cavities 64, 66, as shown in FIGS. 5 and 6. Dial 134 includes mating elements, for example, projections 138, 140 and 142, as shown in FIG. 3. Projection 138 is configured to mate with a selected plate 14, projection 140 is configured to mate with a selected plate 14A and projection 142 is configured to mate with a selected plate 14B, as shown in FIGS. 8 and 12-14. Plate 14 includes a 19 mm dimension, plate 14A includes a 21 mm dimension and plate 14B includes a 23 mm dimension. Indicia, including laser marked wording is disposed on dial 134 below each projection 138, 140, 142 to indicate the dimensions of the selected plate 14, 14A or 14B that is compatible with the selected projection 138, 140 or 142, as shown in FIG. 8. In some embodiments, plate 14, 14A and/or 14B include dimensions of 16 to 26 mm.

Projection 138 engages with a side 144 or a side 146 of plate 14, as shown in FIG. 12. Projection 140 engages with a side 148 or a side 150 of plate 14A, as shown in FIG. 13. Projection 142 engages with a side 152 or a side 154 of plate 14B, as shown in FIG. 14. In some embodiments, sides 144, 146, 148, 150, 152, and/or 154 may comprise overall and/or cross-section configurations, for example, cylindrical, round, oval, rectangular, polygonal, irregular, tapered, offset, staggered, uniform and non-uniform. In some embodiments, sides 144, 146, 148, 150, 152, and/or 154 may include various surface configurations, for example, rough, friction, arcuate, undulating, mesh, porous, semi-porous, dimpled and/or textured according to the requirements of a particular application. In some embodiments, dial 134 includes one projection. In some embodiments, dial 134 includes 1 to 5 projections.

Dial 134 includes a gripping surface 156, as shown in FIG. 3. Gripping surface 156 is configured for engagement with a user for rotating dial 134 to a selected projection 138, 140 or 142 for use with a selected plate 14, 14A or 14B.

Dial 134 is configured for engagement with disc 54 and portions of releasable locks 158, 164 as shown in FIGS. 3, 5 and 7 and described herein. Dial 134 includes a lock spring 160 and a ball bearing 162 configured to lock dial 134 to a locking orientation, to prevent unintentional movement of dial 134 when rotated to a selected projection 138, 140 or 142. A surface of dial 134 defines a centrally disposed opening 157 that includes indents 159, as shown in FIGS. 3, 7 and 8. Indents 159 are configured for locked engagement with ball bearing 162, as described herein to position dial 134 in the locking orientation.

Dial 136 includes mating elements, for example, projections 166, 168 and 170, as shown in FIG. 9. Projection 166 is configured to mate with a selected plate 14, projection 168 is configured to mate with a selected plate 14A and projection 170 is configured to mate with a selected plate 14B, as shown in FIGS. 12-14. Projection 166 engages with side 144 or side 146 of plate 14, as shown in FIG. 12. Projection 168 engages with side 148 or side 150 of plate 14A, as shown in FIG. 13. Projection 170 engages with side 152 or side 154 of plate 14B, as shown in FIG. 14. Indicia, including laser marked text is disposed on dial 136 below each projection 166, 168, 170 to indicate the dimensions of the selected plate 14, 14A or 14B that is compatible with the selected projection 166, 168 or 170, similar to what is shown in FIG. 8 for dial 134. In some embodiments, dial 136 includes one projection. In some embodiments, dial 136 includes 1 to 5 projections.

Dial 136 includes a gripping surface 172, as shown in FIG. 4. Gripping surface 172 is configured for engagement with a user for rotating dial 136 to a selected projection 166, 168 or 170 for use with a selected plate 14, 14A or 14B.

Dial 136 is configured for engagement with disc 60 and a portion of releasable lock 164 as shown in FIGS. 4 and 6 and described herein. Dial 136 includes a lock spring 174 and a ball bearing 176 configured to lock dial 136 in a locking orientation, to prevent unintentional movement of dial 136 when rotated to a selected projection 166, 168 or 170. A surface of dial 136 defines a centrally disposed opening 177 that includes indents 179, as shown in FIG. 4. Indents 179 are configured for locked engagement with ball bearing 176, as described herein to position dial 136 in the locking orientation.

As described above, dial 134 is fixed to implant contouring instrument 12 on the LS and dial 136 is fixed to implant contouring instrument 12 on the KS, as shown in FIGS. 5 and 6. An elongate portion 178 of lock 164 is configured for disposal through opening 177 of dial 136, an opening 182 of disc 60, an opening 184 of link 48, an opening 186 of link 38, an opening 188 of link 46, an opening 190 of disc 54, opening 157 of dial 134 and an opening 194 of an end portion 196 of lock 158, as shown in FIGS. 2-4.

Spring 160 and ball bearing 162 are configured for translation within a recess 198 of end portion 196 and spring 160 is configured for disposal and translation within a recess 200 of elongate portion 178, as shown in FIGS. 7 and 8. Spring 160 and ball bearing 162 are configured to lock dial 134 to the locking orientation when dial 134 is rotated to a selected projection 138, 140 or 142. Dial 134 is rotated to a selected projection 138, 140 or 142 and spring 160 translates ball bearing 162 into an indent 159 to lock dial 134 at a selected projection 138, 140 or 142.

Spring 174 and ball bearing 176 are configured for disposal and translation within a recess 202 of elongate portion 178, as shown in FIG. 4. Spring 174 and ball bearing 176 are configured to lock dial 136 to the locking orientation when dial 136 is rotated to a selected projection 166, 168 or 170. Dial 134 is rotated to a selected projection 166, 168 or 170 and spring 174 translates ball bearing 176 into an indent 179 to lock dial 136 at a selected projection 166, 168 or 170.

Figure 17:
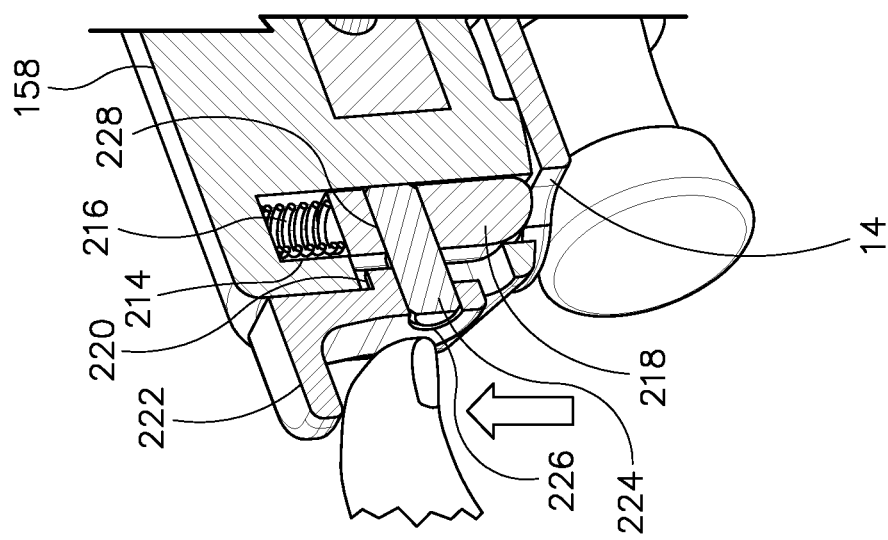
FIG. 17 is a break away view in part cross-section of the components shown in FIG. 16.
Figure 16:
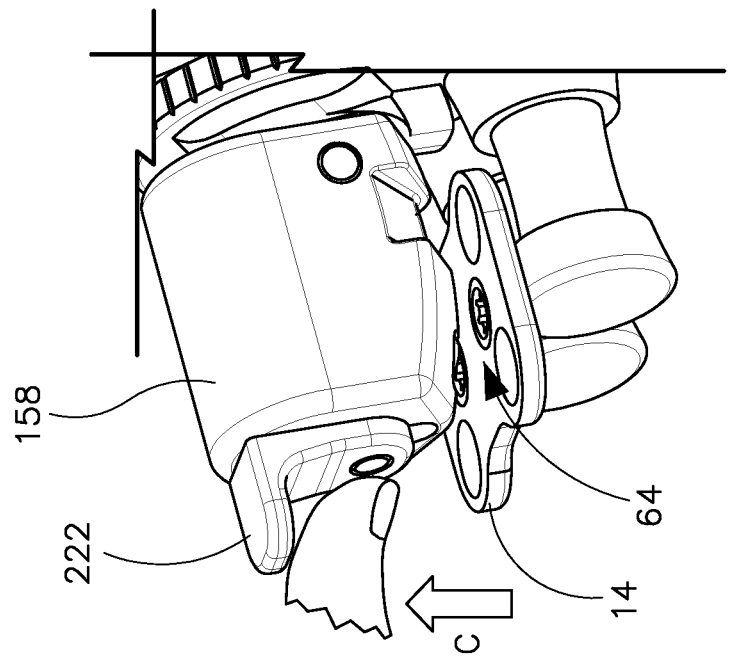
FIG. 16 is a break away view of the components shown in FIG. 1.
Figure 15:
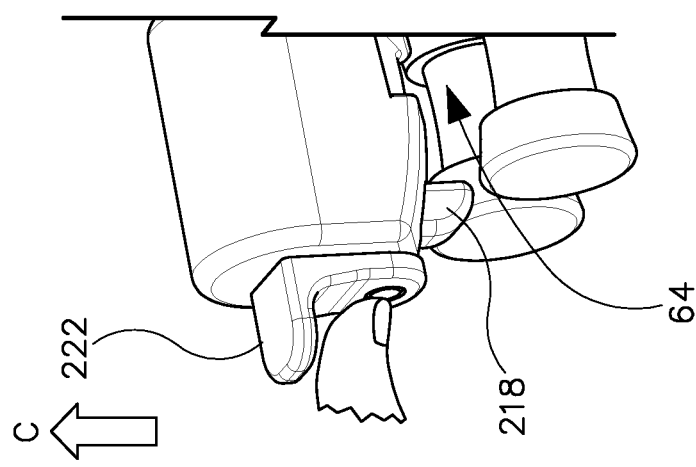
FIG. 15 is a break away view of the components shown in FIG. 1.

Releasable lock 158 is disposed on the LS of implant contouring instrument 12 and is configured to be positioned in a locked orientation to engage with plate 14, 14A or 14B, as shown in FIGS. 18-19 and an unlocked orientation to disengage with plate 14, 14A or 14B, as shown in FIGS. 16-17. Releasable lock 158 is configured for maintaining central or symmetrical alignment of plate 14, 14A or 14B relative to implant contouring instrument 12 during contouring of plate 14, 14A or 14B. Releasable lock 158 includes a housing 204, as shown in FIG. 3. Housing 204 includes an end 205 that includes end portion 196 and a surface that defines a transverse opening 206 that is configured for disposal of a pin 208, as shown in FIGS. 3 and 4. A surface of elongate portion 178 defines a transverse opening 210. Pin 208 is configured for disposal with openings 206, 210 to fix releasable lock 158 with elongate portion 178.

Housing 204 includes an end 212, as shown in FIG. 3. An interior surface of end 212 includes a recess 214 configured for disposal of a spring 216 and a portion of a tab 218, as shown in FIG. 17. An outer surface of end 212 defines a slot 220, as shown in FIGS. 3 and 17. A button, for example, a pull button 222 is engageable with tab 218 via a pin 224. Pin 224 is configured for disposal with an opening 226 of button 222 and an opening 228 of tab 218, as shown in FIGS. 3 and 17. Releasable lock 158 is spring biased in the locked orientation via spring 216. An end 230 of tab 218 is configured for engagement with plate 14, 14A and/or 14B, as shown in FIG. 19.

Releasable lock 164 is disposed on the KS of implant contouring instrument 12 and is configured to be positioned in a locked orientation to engage with plate 14, 14A or 14B, similar to what is shown in FIGS. 18-19 with regard to lock 158 and a non-locked orientation to disengage with plate 14, 14A or 14B, similar to what is shown in FIGS. 16-17 with regard to lock 158. Releasable lock 164 is configured for maintaining central or symmetrical alignment of plate 14, 14A or 14B relative to implant contouring instrument 12 during contouring of plate 14, 14A or 14B. Releasable lock 164 includes a housing 232, as shown in FIG. 4. Housing 232 includes an end 234 that includes elongate portion 178.

Housing 232 includes an end 236, as shown in FIG. 4. An interior surface of end 236 includes a recess (not shown) configured for disposal of a spring 238 and a portion of a tab 240, as shown in FIG. 4. An outer surface of end 236 defines a slot (not shown). A button, for example, a pull button 242 is engageable with tab 240 via a pin 244, as shown in FIG. 6. Pin 244 is configured for disposal with an opening 246 of button 242 and an opening 248 of tab 240, as shown in FIGS. 4 and 6. Releasable lock 164 is spring biased to the locked orientation via spring 238. An end 250 of tab 240 is configured for engagement with plate 14, 14A and/or 14B, similar to what is shown in FIG. 19 with regard to end 230 of tab 218.

In some embodiments, surgical system 10 includes implants, for example, a plurality of bone fasteners (not shown) for attaching plate 14, 14A and/or 14B to vertebrae. In some embodiments, surgical system 10 can include one or a plurality of bone fasteners such as those described herein and/or fixation elements, which may be employed with a single vertebral level. In some embodiments, the bone fasteners and/or fixation elements may be engaged with vertebrae in various orientations, for example, series, parallel, offset, staggered and/or alternate vertebral levels. In some embodiments, the bone fasteners and/or fixation elements may include one or a plurality of anchors, tissue penetrating screws, conventional screws, expanding screws, wedges, anchors, buttons, clips, snaps, friction fittings, compressive fittings, expanding rivets, staples, nails, adhesives, posts, fixation plates and/or posts.

In assembly, operation and use, surgical system 10, similar to that described herein, is employed with a surgical procedure for treatment of a spinal disorder affecting a section of a spine of a patient, as discussed herein. Surgical system 10 may also be employed with other surgical procedures. For example, surgical system 10 can be used with a surgical procedure for treatment of a condition or injury, for example, a correction treatment to treat adolescent idiopathic scoliosis and/or Scheuermann's kyphosis of a spine.

In use, to treat the affected section of vertebrae, a medical practitioner obtains access to a surgical site including vertebrae in any appropriate manner, such as through incision and retraction of tissues. In some embodiments, surgical system 10 may be used in any existing surgical method or technique including open surgery, mini-open surgery, minimally invasive surgery, and percutaneous surgical implantation, whereby vertebrae is accessed through a micro-incision, or sleeve that provides a protected passageway to the area. Once access to the surgical site is obtained, the particular surgical procedure is performed for treating the spinal disorder. Surgical system 10 is then employed to augment the surgical treatment. Pilot holes are made in selected vertebra of vertebrae for receiving bone fasteners. Bone fasteners are fastened with plate 14, 14A and/or 14B and the vertebra or vertebrae.

During the surgical procedure, the contour of vertebrae and/or other portions of an anatomy of a patient selected for disposal and/or attachment of an implant, for example, plate 14, 14A and/or 14B, can be measured and/or determined in situ. In one embodiment, the contour measurement, which may include implant geometry, relative angular orientation of the implant to vertebrae and/or respective portions of the implant, can be measured and/or determined using medical imaging, x-ray, surgical navigation, gauges, provisional, working and/or trial implants and treated using implant contouring instrument 12.

Figure 21:
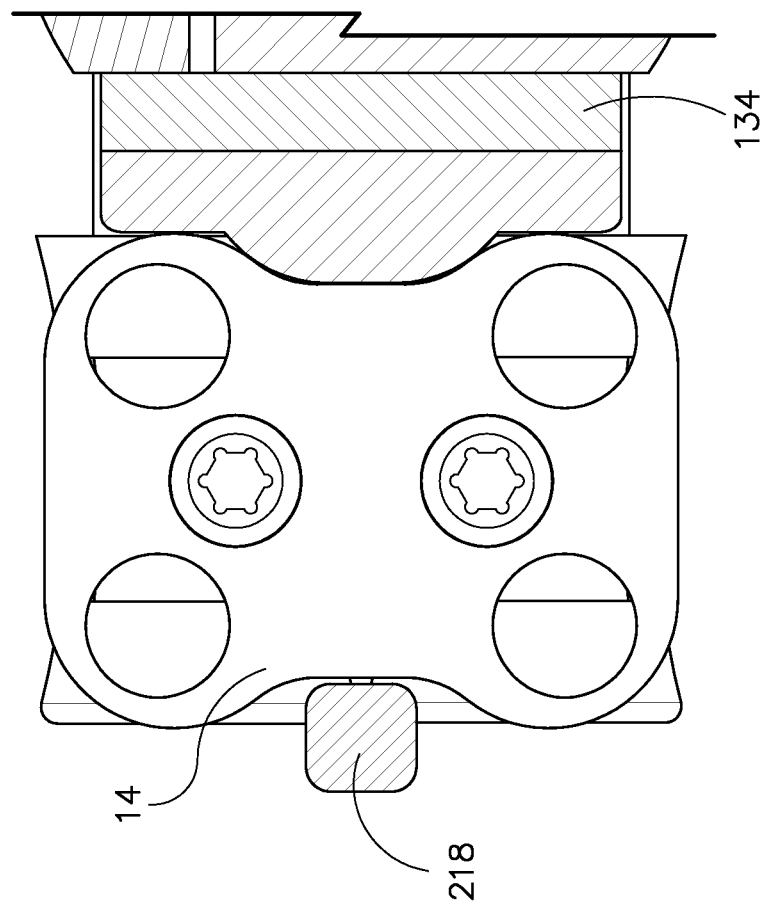
FIG. 21 is a break away view in part cross-section of the components shown in FIG. 20.
Figure 20:
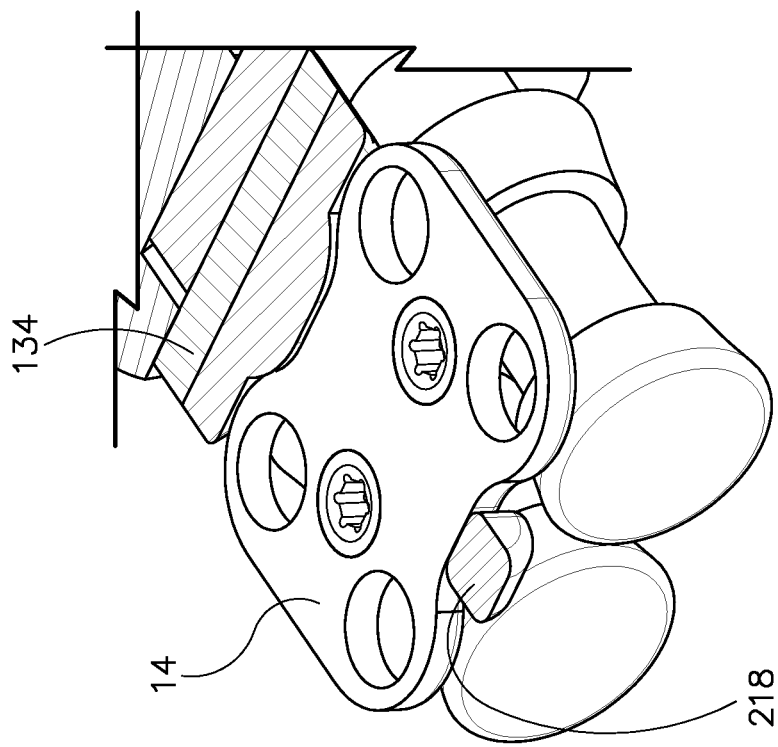
FIG. 20 is a break away view in part cross-section of components of the system shown in FIG. 1.

In one embodiment, implant contouring instrument 12, similar to that described, is used to contour plates 14, 14A and/or 14B in a deformity correction procedure, which includes in situ coronal bending for residual coronal or sagittal deformity. For example, to contour plate 14, 14A or 14B, implant contouring instrument 12 is positioned in an open orientation, as shown in FIG. 10. In the open orientation, arms 16, 18 are spaced apart and ends 20, 28 of arms 16, 18 are in flush engagement relative to each other. A plate size is selected from plates 14, 14A and 14B. To increase lordosis of a selected plate 14, 14A or 14B, dial 134 is rotated in a direction, for example a clockwise direction as shown by arrow A or an anti-clockwise direction as shown by arrow B in FIG. 10 until a selected plate size indicia is aligned and selected. Dial 134 locks into position as described herein. Plate 14, 14A or 14B is selected and button 222 is translated in a direction, for example, an upward direction as shown by arrow C in FIGS. 15 and 16 to lift tab 218 in the upward direction shown by arrow C. Plate 14, 14A or 14B is inserted into cavity 64, as shown in FIG. 16. Button 222 is released and tab 218 is translated in a direction, for example, a downward direction shown by arrow D as shown in FIGS. 18 and 19. In some embodiments, the medical practitioner visually confirms that button 222 is fully released into its original orientation. In some embodiments, the selected plate 14, 14A or 14B is manually adjusted by the medical practitioner to ensure proper engagement of plate 14, 14A or 14B within cavity 64 where plate 14, 14A or 14B is flush with a selected projection 138, 140, 142 and tab 218, as shown in FIGS. 20 and 21.

Figure 24:
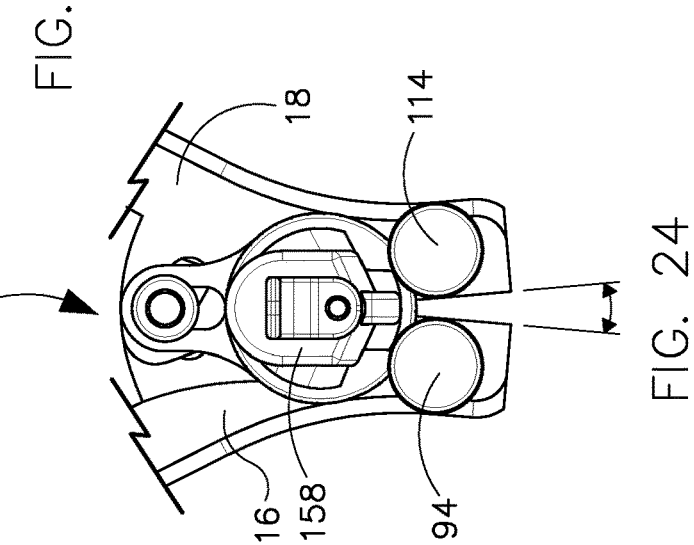
FIG. 24 is a break away view of components shown in FIG. 22.
Figure 22:
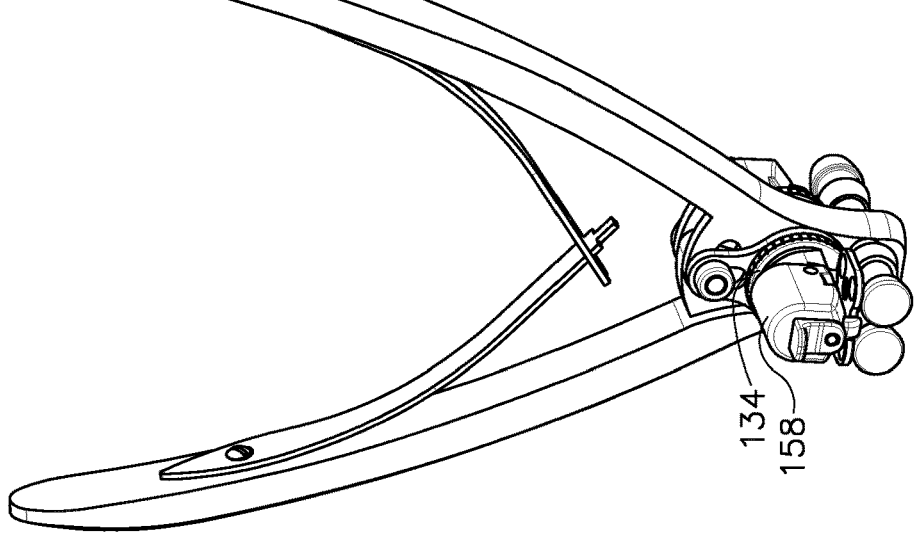
FIG. 22 is a perspective view of components of the system shown in FIG. 1.
Figure 28:
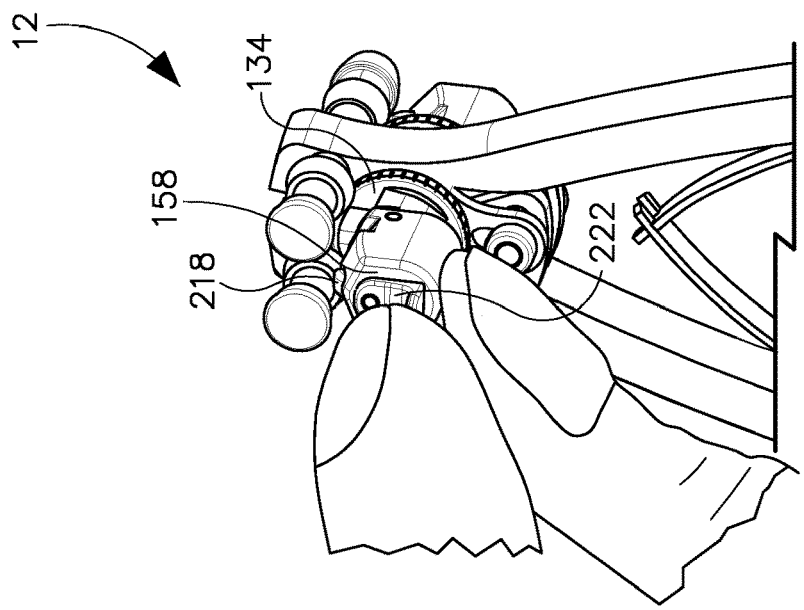
FIG. 28 is a break away view of components shown in FIG. 26.
Figure 27:
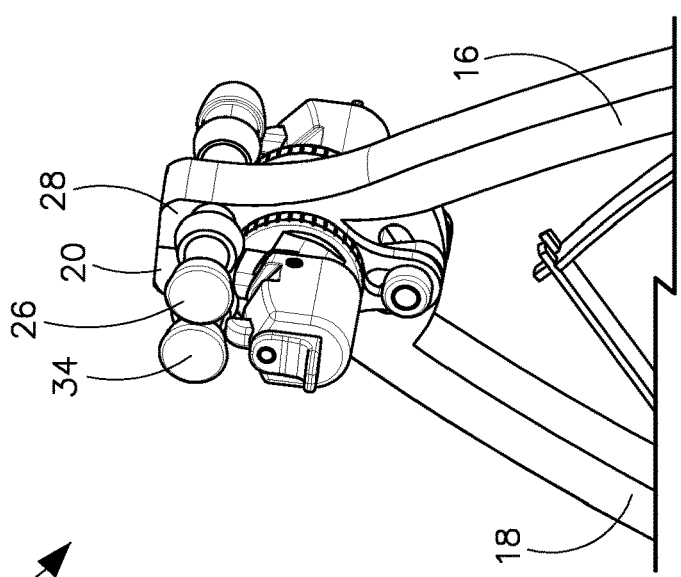
FIG. 27 is a break away view of components shown in FIG. 26.
Figure 26:
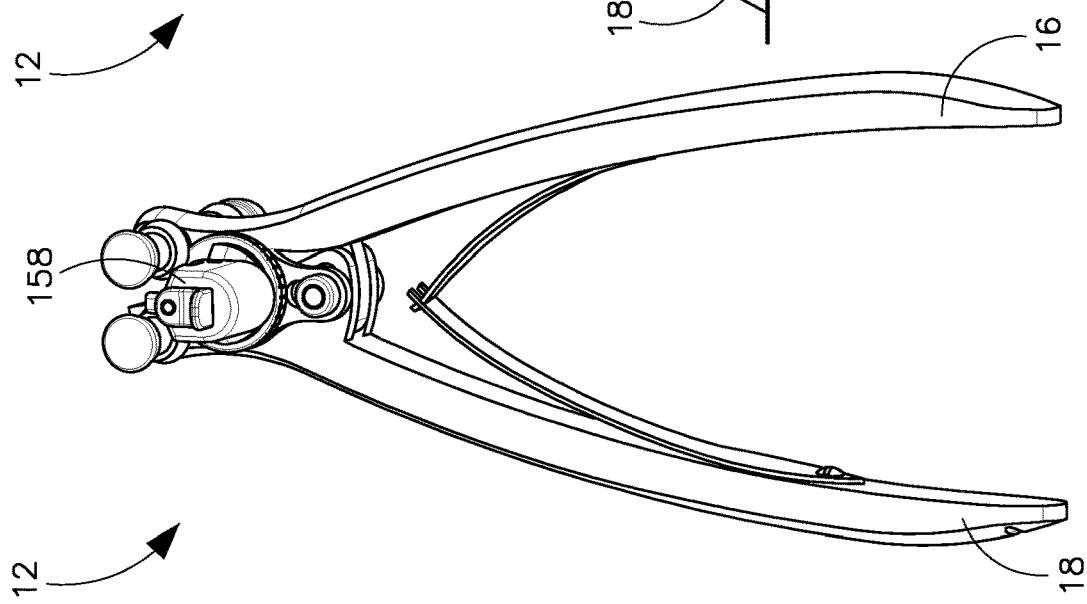
FIG. 26 is a perspective view of components of the system shown in FIG. 1.

Implant contouring instrument 12 is positioned in the closed orientation to contour plate 14, 14A or 14B to a selected curvature/angle to increase lordosis of plate 14, 14A or 14B, as shown in FIGS. 24 and 25. In the closed orientation, arms 16, 18 are translated in a direction, for example, an inward direction as shown by arrows E in FIG. 22 and ends 20, 28 of arms 16, 18 are translated in a direction, for example, an outward direction shown by arrows F in FIG. 25. Fulcrum 36 coupled with surface 94 of transverse roller 26 and surface 114 of transverse roller 34 contour plate 14, 14A or 14B as ends 20, 28 are translated in the outward direction. When the desired lordosis is reached, continued translation of arms 16, 18 is prevented via stop element 57, as shown in FIG. 25. Button 222 is translated in the upward direction of arrow C in FIGS. 15 and 16 to translate tab 218 such that plate 14, 14A or 14B can be removed from implant contouring instrument 12. To decrease lordosis of plate 14, 14A or 14B, the steps described above are repeated on the KS of implant contouring instrument 12 specific to decreasing the lordotic angle of plate 14, 14A or 14B.

In some embodiments, surgical system 10 includes an agent, which may be disposed, packed or layered within, on or about the components and/or surfaces of surgical system 10. In some embodiments, the agent may include bone growth promoting material, for example, bone graft to enhance fixation of bone fasteners with vertebrae. In some embodiments, the agent may include one or a plurality of therapeutic agents and/or pharmacological agents for release, including sustained release, to treat, for example, pain, inflammation and degeneration.

The components of surgical system 10 can be made of radiolucent materials such as polymers. Radiomarkers may be included for identification under x-ray, fluoroscopy, CT or other imaging techniques. In some embodiments, the use of microsurgical and image guided technologies may be employed to access, view and repair spinal deterioration or damage, with the aid of surgical system 10. Upon completion of the procedure, the surgical instruments, assemblies and non-implant components of surgical system 10 are removed from the surgical site and the incision is closed.

In one embodiment, as shown in FIGS. 29-32, surgical system 10, similar to the systems and methods described above with regard to FIGS. 1-28, includes an implant contouring instrument 312, similar to implant contouring instrument 12 described herein. Implant contouring instrument 312 is employed, for example, to contour an implant, for example, plate 14, 14A and/or 14B during a surgical treatment to the configuration and/or dimension of the spine to increase or decrease lordosis, as described herein. In some embodiments, lordosis is increased from 1 to 30 degrees and kyphosis is decreased from 1 to 30 degrees, as described herein.

Figure 29:
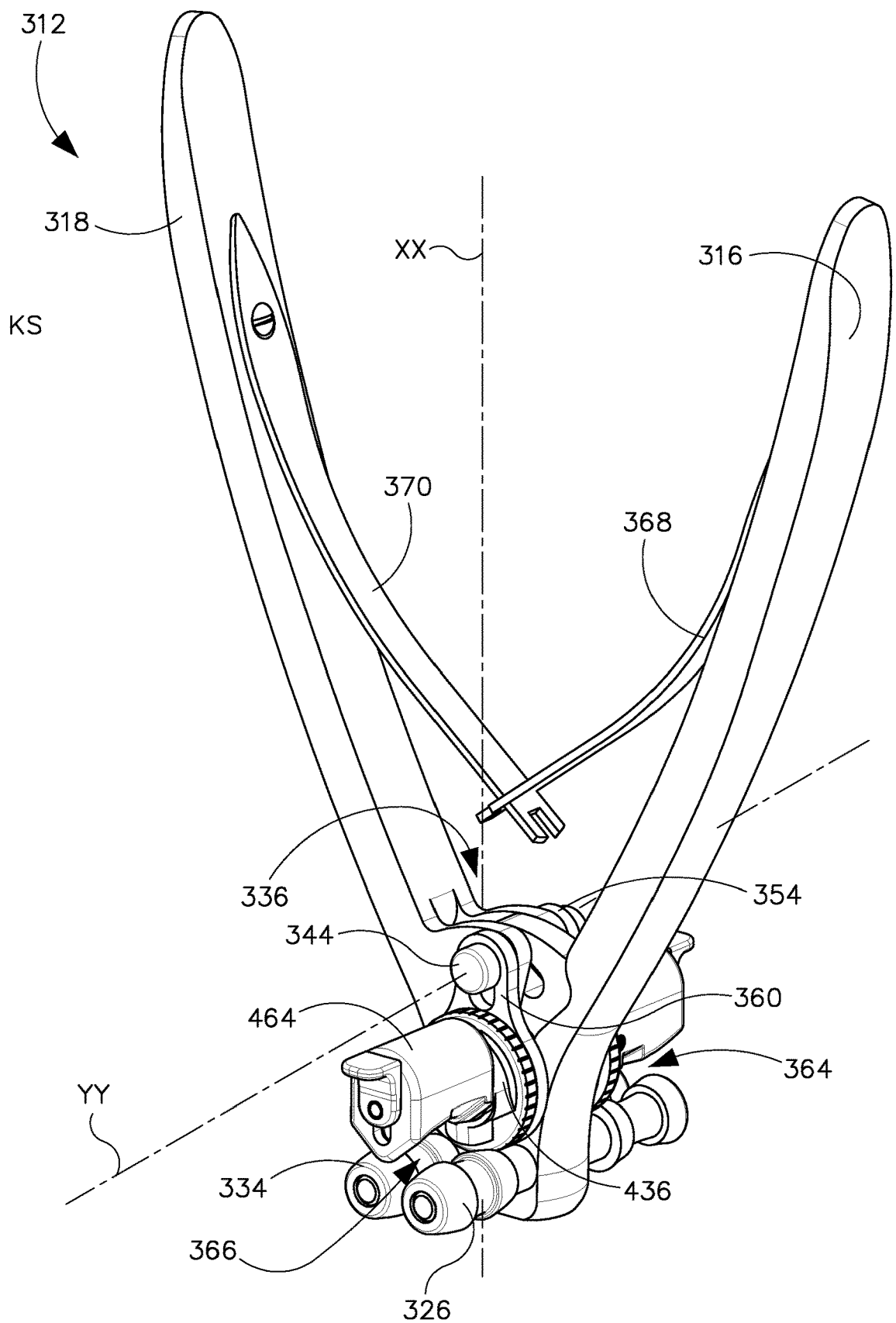
FIG. 29 is a perspective view of one embodiment of components of a surgical system in accordance with the principles of the present disclosure.

Implant contouring instrument 312 defines a longitudinal axis XX, as shown in FIG. 29 and includes an arm 316 and an arm 318, as shown in FIG. 29 and similar to arms 16, 18 described above with regard to implant contouring instrument 12. Arms 316, 318 are configured to be pivotable between an open and a closed orientation relative to each other to move a fulcrum 336 of implant contouring instrument 312 to facilitate contouring of plate 14, 14A or 14B as described herein. Arm 316 extends between an end 320 and an end 322. End 320 includes a surface that defines an opening 324 configured for disposal of a portion of a support, for example, a portion of a transverse roller 326, as shown in FIG. 29 and described herein. Arm 318 extends between an end 328 and an end 330. End 328 includes a surface that defines an opening 332 configured for disposal of a portion of a support, for example, a portion of a transverse roller 334, as shown in FIG. 29 and described herein.

Fulcrum 336 defines a longitudinal axis YY, as shown in FIG. 29 and is configured to translate relative to transverse rollers 326, 334 to engage plate 14, 14A or 14B and to contour plate 14, 14A or 14B to a selected lordosis and/or kyphosis. Transverse rollers 326, 334 are similar to transverse rollers 26, 34 described above with regard to implant contouring instrument 12. Fulcrum 336 includes a link 338 defined from a surface of arm 316, as shown in FIGS. 30 and 31. Link 338 is configured for disposal within a slot 340 of arm 318, as described herein for pivotable engagement between arms 316, 318. Link 338 includes a surface that defines an opening 342. Opening 42 is configured for disposal with a pin 344 of fulcrum 336, as shown in FIG. 29. Fulcrum 336 includes a link 346 and a link 348 defined from surfaces of arm 318, as shown in FIG. 30. Link 346 is parallel relative to link 348. Slot 340 is defined from an interior of links 346, 348. Link 346 includes a surface that defines an opening 350 and link 348 includes a surface that defines an opening 352. Openings 350, 352 are configured for disposal with pin 344, as shown in FIG. 29. Links 338, 346 and 348 are disposed at an angle α2 to facilitate contouring of plate 14, 14A or 14B at an angle from 1 degree to 30 degrees, as shown in FIGS. 30 and 31.

Figure 32:
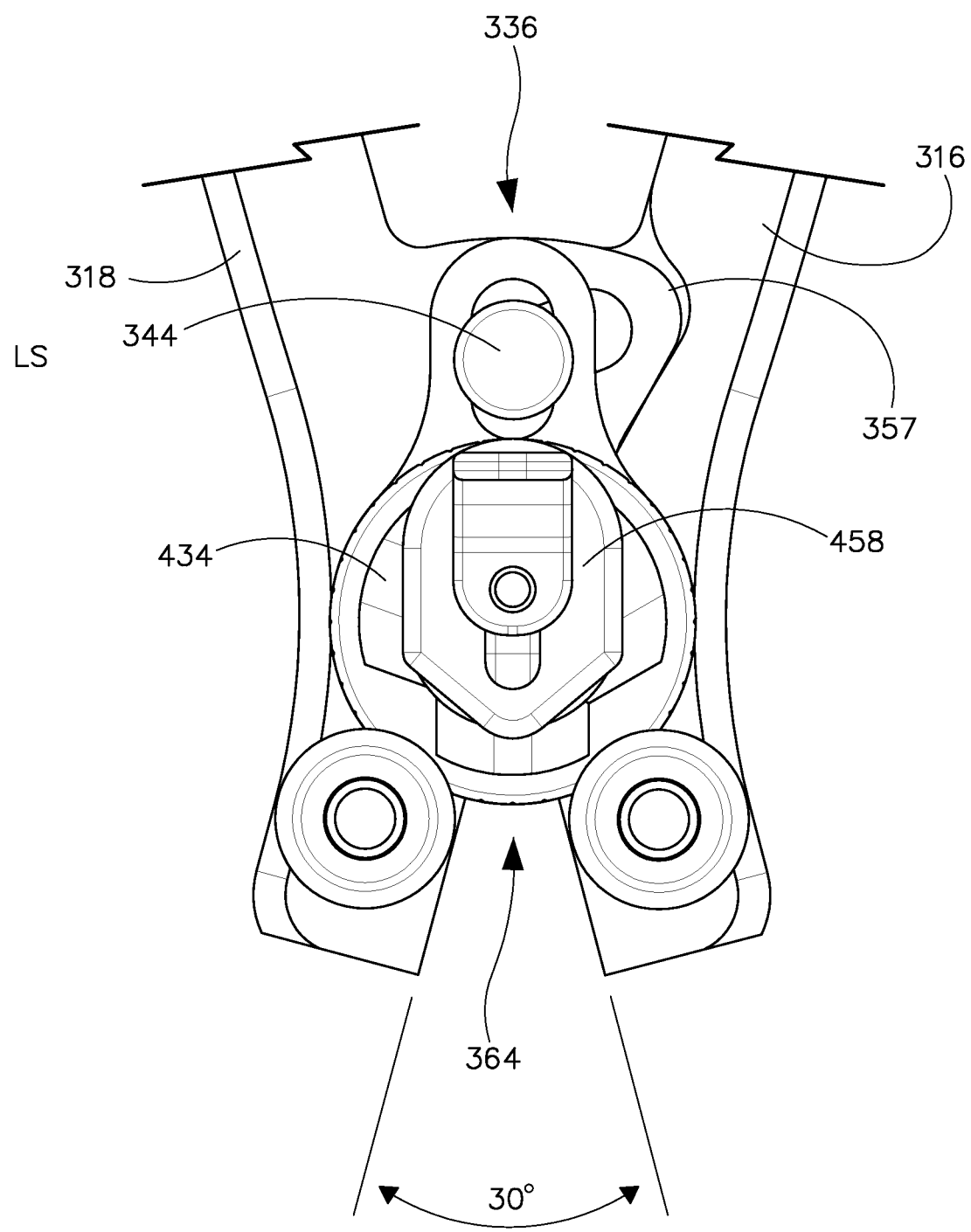
FIG. 32 is a break away view of components shown in FIG. 29.

Fulcrum 336 includes a disc 354 and a disc 360 similar to discs 54 and 60 described above with regard to implant contouring instrument 12. A stop element 357, as shown in FIG. 32 is similar to stop element 57 described above with regard to implant contouring instrument 12. Stop element 357 is configured to limit implant contouring instrument 312 from contouring plate 14, 14A or 14B beyond 30 degrees.

Fulcrum 336 defines an implant cavity 364 with transverse rollers 326, 334 on a lordosis surface (LS) of implant contouring instrument 312, as shown in FIG. 32, and an implant cavity 366 on a kyphosis surface (KS) of implant contouring instrument 312, as shown in FIG. 29. Arm 316 and/or arm 318 includes indicia, for example, laser markings including text that indicates the KS or the LS of implant contouring instrument 312, similar to the laser markings described above with regard to implant contouring instrument 12. In some embodiments, the LS is a side of implant contouring instrument 312 and the KS is an opposing side of implant contouring instrument 312. Implant contouring instrument 312 includes flat springs 368 and 370, rotatable dials 434, 436 and releasable locks 458, 464, similar to flat springs 68, 70, rotatable dials 134, 136 and releasable locks 158, 164 described above with regard to implant contouring instrument 12.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a first arm including a first support extending from a first side of the first arm and a second support extending from an opposite second side of the first arm;
   a second arm including a third support extending from a first side of the second arm and a fourth support extending from an opposite second side of the second arm;
   a fulcrum comprising a plate, the plate directly engaging the first sides, the fulcrum defining an implant cavity with the first and third supports; and
   a member selectively engageable with alternatively configured and dimensioned implants disposable in the implant cavity, the member comprising a rotatable dial and a releasable lock, the releasable lock comprising a first housing an elongated portion extending from the first housing, the elongated portion extending through the arms and the plate, the releasable lock comprising a second housing coupled to the elongated portion and a tab coupled to the second housing, the tab being configured for engagement with the implants, the dial being positioned between the plate and the second housing.

2. A surgical instrument as recited in claim 1, wherein the arms are pivotable between an open orientation and a closed orientation to move the fulcrum relative to the supports.

3. A surgical instrument as recited in claim 2, wherein the arms are biased to the open orientation.

4. A surgical instrument as recited in claim 1, wherein the fulcrum translates relative to the supports to engage the implant and to deform the implant to a selected lordosis and kyphosis.

5. A surgical instrument as recited in claim 1, wherein the supports each include a transverse roller.

6. A surgical instrument as recited in claim 5, wherein each of the transverse rollers of the first and third supports include a lordosis portion and the transverse rollers of the second and fourth supports define a kyphosis portion.

7. A surgical instrument as recited in claim 1, wherein the dial includes mating elements having at least a first projection configured to mate with a first selected implant and a second projection configured to mate with a second selected implant.

8. A surgical instrument as recited in claim 1, wherein the dial includes mating elements having at least a first projection configured to mate with a first selected implant, a second projection configured to mate with a second selected implant; and a third projection configured to mate with a third selected implant.

9. A surgical instrument as recited in claim 8, wherein the first selected implant includes a 19 mm dimension, the second selected implant includes a 21 mm dimension, and the third selected implant includes a 23 mm dimension.

10. A surgical instrument as recited in claim 1, wherein the dial includes mating elements.

11. A surgical instrument as recited in claim 10, wherein the dial has a gripping surface.

12. A surgical instrument as recited in claim 10, wherein the dial is rotatable to one or a plurality of the mating elements.

13. A surgical instrument as recited in claim 12, wherein the dial includes a lock-spring biased to a locking orientation when the dial is rotated to one of the plurality of mating elements.

14. A surgical instrument as recited in claim 1, wherein the tab is movable relative to the second housing.

15. A surgical instrument as recited in claim 1, wherein the releasable lock is configured to be positioned in a locked orientation and a non-locked orientation.

16. A surgical instrument as recited in claim 15, wherein the releasable lock is spring biased in the locked orientation.

17. A surgical instrument as recited in claim 1, wherein the second housing defining a recess, the tab and a spring being positioned in the recess to move the tab relative to the second housing.

18. A surgical instrument comprising:
a first arm including a first support extending from a first side of the first arm and a second support extending from an opposite second side of the first arm;
a second arm including a third support extending from a first side of the second arm and a fourth support extending from an opposite second side of the second arm; and
a fulcrum comprising a plate, the plate directly engaging the first sides, the fulcrum defining an implant cavity with the first and third supports; and
a member directly selectively engageable with alternatively configured and dimensioned implants disposable in the implant cavity, the member comprising a rotatable dial and a releasable lock, the releasable lock comprising a first housing an elongated portion extending from the first housing, the elongated portion extending through the arms and the plate, the releasable lock comprising a second housing coupled to the elongated portion and a tab movably positioned in a recess of the second housing, the tab being configured for engagement with the implants, the dial being positioned between the plate and the second housing, the releasable lock being configured to be positioned in a locked orientation and a non-locked orientation.

19. A surgical instrument as recited in claim 18, wherein the dial includes an adjustable mating element engageable with an implant.

20. A surgical system comprising:
a surgical instrument comprising a first arm including a first support extending from a first side of the first arm and a second support extending from an opposite second side of the first arm, the instrument comprising a second arm including a third support extending from a first side of the second arm and a fourth support extending from an opposite second side of the second arm, the instrument comprising a fulcrum comprising a plate, the plate directly engaging the first sides, the fulcrum defining an implant cavity with the first and third supports, the instrument comprising a member selectively engageable with alternatively configured and dimensioned implants disposable in the implant cavity, the member comprising a rotatable dial and a releasable lock, the releasable lock comprising a first housing an elongated portion extending from the first housing, the elongated portion extending through the arms and the plate, the releasable lock comprising a second housing coupled to the elongated portion and a tab movably positioned in a recess of the second housing, the tab being configured for engagement with the implants, the dial being positioned between the plate and the second housing, the dial including an adjustable mating element; and
a spinal plate engageable with the adjustable mating element.

* * * * *